United States Patent
Miller et al.

(10) Patent No.: US 10,130,343 B2
(45) Date of Patent: *Nov. 20, 2018

(54) INTRAOSSEOUS NEEDLE SETS

(71) Applicant: TELEFLEX MEDICAL DEVICES S.A.R.L, Luxembourg (LU)

(72) Inventors: Larry J. Miller, Shavano Park, TX (US); Robert W. Titkemeyer, Shavano Park, TX (US); John Morgan, San Antonio, TX (US); Christopher Kilcoin, South Lake Tahoe, CA (US)

(73) Assignee: TELEFLEX MEDICAL DEVICES S.À R.L., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,213

(22) Filed: Aug. 15, 2016

(65) Prior Publication Data
US 2017/0035397 A1     Feb. 9, 2017

Related U.S. Application Data

(63) Continuation of application No. 13/835,046, filed on Mar. 15, 2013, now Pat. No. 9,414,815.

(51) Int. Cl.
*A61B 5/00*     (2006.01)
*A61B 10/02*    (2006.01)
(Continued)

(52) U.S. Cl.
CPC ........ *A61B 10/025* (2013.01); *A61B 10/0266* (2013.01); *A61B 17/1613* (2013.01);
(Continued)

(58) Field of Classification Search
CPC . A61B 10/02; A61B 10/0233; A61B 10/0266; A61B 10/0241; A61B 10/025; A61B 2010/0258; A61B 5/02
See application file for complete search history.

(56) References Cited

U.S. PATENT DOCUMENTS

| | | |
|---|---|---|
| 4,258,722 A | 3/1981 | Sessions |
| 4,543,966 A | 10/1985 | Islam |

(Continued)

FOREIGN PATENT DOCUMENTS

| | | |
|---|---|---|
| EP | 1175870 A1 | 1/2002 |
| WO | 2005/009246 A1 | 2/2005 |

(Continued)

OTHER PUBLICATIONS

International Search Report and Written Opinion issued for International Patent Application No. PCT/US2014/028564, dated Aug. 28, 2014.

*Primary Examiner* — Max Hindenburg
(74) *Attorney, Agent, or Firm* — Baker Hostetler LLP

(57) ABSTRACT

An intraosseous needle set comprising a cannula is provided. The cannula has a first end, a second end, and a bore configured to receive a sample from a target area. The first end of the cannula is configured to penetrate the target area and has a plurality of teeth. The plurality of teeth may have at least one tooth that comprises a tapered surface. The plurality of teeth may each have a first side and a second side, where a length of the first side is less than a length of the second side. The first and second sides may intersect to define tips that are disposed at an angle between 0 and 30 degrees relative to a longitudinal axis of the cannula, and the first side of a first tooth and the second side of an adjacent tooth may also intersect at an angle between 55 and 80 degrees.

20 Claims, 19 Drawing Sheets

DETAIL N

(51) Int. Cl.
    *A61B 17/16*     (2006.01)
    *A61B 5/02*     (2006.01)

(52) U.S. Cl.
    CPC ............. *A61B 5/02* (2013.01); *A61B 10/0233* (2013.01); *A61B 2010/0258* (2013.01)

(56) References Cited

U.S. PATENT DOCUMENTS

| | | |
|---|---|---|
| 4,708,147 A | 11/1987 | Haaga |
| 5,183,053 A | 2/1993 | Yeh et al. |
| 5,271,414 A | 12/1993 | Partika |
| 5,807,277 A | 9/1998 | Swaim |
| 5,817,071 A | 10/1998 | Dewindt et al. |
| 6,080,115 A | 6/2000 | Rubinstein |
| 6,443,910 B1 | 9/2002 | Krueger |
| 7,018,343 B2 | 3/2006 | Plishka |
| 7,455,645 B2 | 11/2008 | Goldenberg |
| 7,744,544 B2 | 6/2010 | Ward et al. |
| 7,850,620 B2 | 12/2010 | Miller |
| 7,998,086 B2 | 8/2011 | Boock |
| 8,002,733 B2 | 8/2011 | Kraft |
| 8,251,915 B2 | 8/2012 | Dunn |
| 8,641,715 B2 | 2/2014 | Miller |
| 9,414,815 B2 * | 8/2016 | Miller ................ A61B 10/025 |
| 2003/0236506 A1 | 12/2003 | Schofield |
| 2005/0009246 A1 | 2/2005 | Malagoli |
| 2010/0204611 A1 | 8/2010 | Zambelli |
| 2011/0082387 A1 | 4/2011 | Miller |
| 2011/0306841 A1 | 12/2011 | Lozman |
| 2012/0165832 A1 | 6/2012 | Oostman |

FOREIGN PATENT DOCUMENTS

| | | |
|---|---|---|
| WO | 2008033874 A2 | 3/2008 |
| WO | 2008/115526 A2 | 9/2008 |

* cited by examiner

DETAIL K

DETAIL M

DETAIL N

INTRAOSSEOUS NEEDLE SETS

RELATED APPLICATIONS

The present application is a continuation of U.S. patent application Ser. No. 13/835,046, filed Mar. 15, 2013, the entire contents of which is incorporated herein by reference.

BACKGROUND

The present invention relates generally to intraosseous needle sets and kits comprising intraosseous needle sets, among other things, and more particularly, but not by way of limitation, to intraosseous needle sets having a non-circular bore configured to receive a sample from a target area (e.g., a cortex, a sternum, a humerus, and/or the like).

Examples of intraosseous needle sets are disclosed, for example, in U.S. Pat. Nos. 5,807,277; 7,455,645; and 8,002,733.

SUMMARY

This disclosure includes embodiments of intraosseous needle sets and kits comprising intraosseous needle sets, among other things. The intraosseous needle sets of this disclosure can have a non-circular bore configured, for example, to receive a sample from a target area (e.g., a cortex, a sternum, a humerus, and/or the like).

Some embodiments of the present intraosseous needle sets comprise a cannula having a first end, a second end, and a bore configured to receive a sample from a target area, the bore having: a length extending from the second end of the bore through the first end; a circular cross-section with a substantially constant diameter along a majority a the length of the bore; and a non-circular cross-section along a minority of the length of the bore and closer to the first end than the second end. In some embodiments, the non-circular cross-section extends from the first end toward the second end. In some embodiments, the non-circular cross-section has a first transverse dimension and a second transverse dimension that is different than the first transverse dimension. In some embodiments, the first transverse dimension is greater than the second transverse dimension.

In some embodiments, the cannula can rotatably penetrate the target area to receive a sample having a circular cross-section with a substantially constant diameter. In some embodiments, the cross-section of the sample has a transverse dimension substantially equal to the second transverse dimension of the non-circular cross-section of the bore. In some embodiments, the first end of the cannula comprises at least one cutting surface configured to penetrate the target area. In some embodiments, the first end of the cannula comprises a plurality of crowns having at least one cutting surface between adjacent crowns, where the crowns and the cutting surfaces are configured to penetrate the target area. In some embodiments, the first end of the cannula comprises a plurality of teeth each having a tip. In some embodiments, each of the plurality of teeth comprises a first side and a second side. In some embodiments, a length of the first side of each tooth is less than a length of the second side. In some embodiments, the tip of each of the plurality of teeth is defined by an intersection of the first side and the second side of that tooth. In some embodiments, a first side of a first tooth intersects a second side of an adjacent tooth.

Some embodiments of the present intraosseous needle sets comprise a stylet having a first end and a second end, where the stylet is configured to be disposed in the bore of the cannula such that the first end of the stylet cooperates with the first end of the cannula to define a tip for penetrating the target area. In some embodiments, the stylet is configured to be disposed in the cannula such that the first end of the stylet and the first end of the cannula cooperate to form a cutting surface. In some embodiments, the cutting surface is substantially planar. In some embodiments the first end of the stylet comprises at least one tip; at least one first tapered cutting surface extending a first length from the at least one tip; and at least one second tapered cutting surface extending a second length from the at least one tip, where the length of the first tapered cutting surface is less than the length of the second tapered cutting surface. In some embodiments, the first end of the stylet comprises a surface configured to evacuate a sample from the bore.

Some embodiments of the present intraosseous needle sets comprise a first hub having a first end and a second end, where the first end is configured to be coupled to the second end of the cannula. In some embodiments, the first end of the first hub comprises a depth limiter configured to limit the depth to which at least one of the cannula and the stylet can enter the target area.

Some embodiments of the present intraosseous needle sets comprise a second hub having a first end and a second end, the first end configured to be coupled to the second end of the stylet and further configured to be releasably coupled to the second end of the first hub. In some embodiments, the second hub is configured to be coupled to the first hub by a Luer lock fitting.

Some embodiments of the present intraosseous needle sets comprise a manual driver comprising a handle and a drive shaft configured to be releasably coupled to at least one of the first hub and the second hub. In some embodiments, the intraosseous needle sets comprise a powered driver comprising a housing having a handle; a drive shaft configured to be coupled to at least one of the first hub and the second hub; a motor coupled to the drive shaft; a power source coupled to the motor; and a trigger coupled to the motor, the trigger configured to actuate the motor to move the drive shaft such that at least one of the stylet and the cannula can penetrate the target area. In some embodiments, the motor is configured to rotate the drive shaft about an axis of rotation. In some embodiments, the motor is configured to move the drive shaft longitudinally with respect to the housing. In some embodiments, the power source comprises a battery. In some embodiments, the motor is further configured to remove at least one of the stylet and the cannula from the target area.

Some embodiments of the present intraosseous needle sets comprise a coupler having a first end and a second end, the first end of the coupler configured to be coupled to at least one of the first hub and the second hub, the second end of the coupler configured to be coupled to the drive shaft. In some embodiments, the coupler comprises a depth limiter configured to limit the depth to which at least one of the cannula and the stylet can penetrate the target area.

Some embodiments of the present kits include at least one cannula having a first end, a second end, and a bore configured to receive a sample from a target area, the bore having a length extending from the second end of the bore through the first end; a circular cross-section with a substantially constant diameter along a majority of the length of the bore; and a non-circular cross-section along a minority of the length of the bore and extending through the first end. In some embodiments, the kits comprise at least one stylet configured to be at least partially disposed within the bore of the cannula and further configured to cooperate with the first end of the cannula to penetrate the target area. In some embodiments, the kits comprise at least one of a powered driver and a manual driver configured to be coupled to at least one of the cannula and the stylet. In some embodiments, the kits comprise a coupler having a first end and a second end, the first end configured to be coupled to at least one of the cannula and the stylet, the second end configured to be coupled to at least one of the manual driver and the powered driver. In some embodiments, the kits comprise a containment hag configured to receive at least one of a powered and a manual driver so as to prevent desterilization of at least one of the target area, the cannula, and the stylet. In some embodiments, the kits comprise at least one sharps protector configured such that at least one of the cannula and the stylet can be disposed in the sharps protector to prevent exposure of a cutting surface.

Some embodiments of the present methods of manufacturing an intraosseous needle set comprise configuring a cannula to have a first end, a second end, and a bore configured to receive a sample from a target area in a human; shaping the first end of the cannula such that the first end comprises at least one cutting surface configured to penetrate the target area; and pinching the cannula such that a portion of the bore of the cannula comprises a circular cross-section and another portion of the bore comprises a non-circular cross-section. In some embodiments the first end of the cannula comprises the non-circular cross-section. In some embodiments, the non-circular cross-section extends along a minority of the length of the bore. In some embodiments, the non-circular cross-section has a first transverse dimension and a second transverse dimension that is different than the first transverse dimension. In some embodiments, the first transverse dimension is greater than the second transverse dimension. In some embodiments, the cannula can rotatably penetrate the target area to receive a sample having a circular cross-section with a substantially constant diameter. In some embodiments, the cross-section of the sample has a transverse dimension substantially equal to the second transverse dimension of the non-circular cross-section of the bore.

Any embodiment of any of the present intraosseous needle sets and kits can consist of or consist essentially of—rather than comprise/include/contain/have—any of the described elements and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures illustrate the described elements using graphical symbols that will be understood by those of ordinary skill in the art. The embodiments of the present intraosseous needle sets and kits and their components shown in the figures are drawn to scale for at least the embodiments shown.

DESCRIPTION OF ILLUSTRATIVE EMBODIMENTS

Figure 1A:
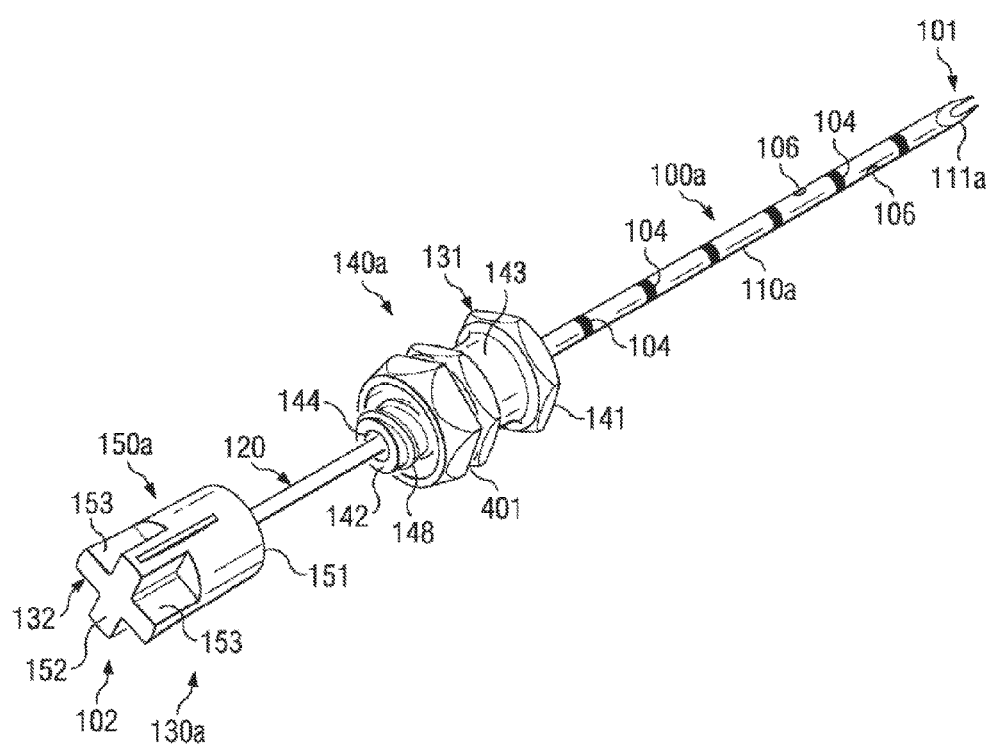
FIG. 1A depicts a perspective view of a prior art intraosseous device having a cannula and a stylet.

The term "coupled" is defined as connected, although not necessarily directly, and not necessarily mechanically. Two items are "couplable" if they can be coupled to each other. Unless the context explicitly requires otherwise, items that are couplable are also decouplable, and vice versa. One non-limiting way in which a first structure is couplable to a second structure is for the first structure to be configured to be coupled to the second structure. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially,"

"approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result an intraosseous needle set or kit, or a component of an intraosseous needle set or kit, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

Further, an intraosseous needle set or kit configured in a certain way is configured in at least that way, but can also be configured in other ways than those specifically described.

Various types of coupler assemblies incorporating teachings of the present disclosure may be satisfactorily used to releasably engage one end of a shaft extending from a driver with one end of an intraosseous device. For some embodiments the powered driver may include a driveshaft having one end with a generally hexagonal cross section operable to be releasably engaged with a latch mechanism disposed in one end of a coupler assembly. For some embodiments a coupler assembly incorporating teachings of the present disclosure may be referred to as a "hands free" coupler, a quick disconnect or quick release coupler and/or port assembly.

Embodiments of the present powered drivers may be used to insert an IO device into a selected target area or target site in ten seconds or less. However, various teachings of the present disclosure are not limited to use with powered drivers. Manual drivers and spring powered drivers may also be used with IO devices (e.g., such as embodiments of the present intraosseous needle sets) incorporating teachings of the present disclosure.

Examples of manual drivers are shown in patent application Ser. No. 11/042,912, entitled "Manual Intraosseous Device," filed Jan. 25, 2005, published as U.S. Patent Application Publication No. 2005/0165404, and issued as U.S. Pat. No. 8,641,715. The term "fluid" may be used in this application to include liquids such as, but not limited to, blood, water, saline solutions, IV solutions, plasma, or any mixture of liquids, particulate matter, dissolved medication, and/or drugs associated with biopsy or aspiration of bone marrow or communication of fluids with bone marrow or other target sites. The term "fluid" may also be used in this patent application to include any body fluids and/or liquids containing particulate matter such as bone marrow and/or cells which may be withdrawn from a target area.

The terms "harvest" and "harvesting" may be used in this application to include bone and/or bone marrow biopsy and bone marrow aspiration. Bone and/or bone marrow biopsy (sometimes referred to as "needle biopsy") may be generally described as removing a relatively small piece or specimen of bone and/or bone marrow from a selected target area for biopsy purposes. Bone marrow aspiration (sometimes referred to as "bone marrow sampling") may be generally described as removing larger quantities of bone marrow from a selected target area. Relatively large quantities of bone marrow may be used for diagnostic, transplantation, and/or research purposes. For example some stem cell research techniques may require relatively large quantities of bone marrow.

The term "insertion site" may be used in this application to describe a location on a bone at which an intraosseous device may be inserted or drilled into the bone and associated bone marrow. Insertion sites are generally covered by skin and soft tissue. The term "target area" refers to any location on or within biological material, such as the biological material of a living human being.

The term "intraosseous (IO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, ID needle set, biopsy needle set or aspiration needle set operable to access or provide access to an intraosseous space or interior portions of a bone. Such IO devices may be formed, at least in part, from metal alloys such as 304 stainless steel and other biocompatible materials associated with needles and similar medical devices.

Embodiments of the present intraosseous needle sets can be included in medical procedure trays such as those disclosed in International Patent Application No. PCT/US2007/078207 (published as WO 2008/033874).

The devices and components shown in FIGS. 1A to 7C are prior art devices and components, and the following description of them is provided to give the reader context for the types of devices and components that can be used consistently with embodiments of the present intraosseous needle sets and kits.

Referring now to the drawings, and more particularly to FIG. 1A, shown therein and designated by the reference numeral 100 is one embodiment of the present intraosseous (IO) needle sets or aspiration needle sets. Aspiration needle set 100 comprises a hollow outer penetrator or cannula 110a, a corresponding inner penetrator or stylet (or trocar) 120, and a hub assembly 130a. In the embodiment shown, first end 111a of cannula 110a and first end 121 of stylet 120 are operable or configured to penetrate a bone and associated bone marrow. Various features of first end 111a of cannula 110a and first end 121 of stylet 120 are shown in more detail in. First end 101 of IO needle set 100 corresponds generally with first end 111a of cannula 110a and first end 121 of stylet 120.

In the embodiment shown, cannula 110a includes a plurality of markings 104 disposed on exterior portions of the cannula. Markings 104 may be referred to as "positioning marks" or "depth indicators," and may be used to indicate the depth of penetration of needle set 100 into a bone and associated bone marrow. In some embodiments, cannula 110a may have a length of approximately sixty (60) millimeters and/or a nominal outside diameter of approximately 0.017 inches (e.g., corresponding generally to the dimensions of a sixteen (16) gauge needle). Cannula 110a and/or stylet 120 may be formed from stainless steel or other suitable biocompatible materials. In some embodiments, markings 104 are spaced at one (1) centimeter intervals on exterior portions of cannula 110a. In some embodiments, one or more side ports 106 may be formed in exterior portions of cannula 110a spaced from first end 111a.

Hub assembly 130a may be configured and/or used to releasably dispose stylet 120 within the longitudinal bore or lumen of cannula 110a. In the embodiment shown, hub assembly 130a includes a first hub 140a and a second hub 150a. A second end of cannula 110a, opposite from first end 111*a*, may be securely engaged with hub 140*a*. The second end of stylet 120, opposite from first end 121, may be securely engaged with the first end of hub 150*a*. As shown in FIG. 1A, cannula 110*a* may extend longitudinally from first end 141 of hub 140*a*. Stylet 120 may also extend from the first end of hub 150*a*. The second end of hub 140*a* may include a standard Luer lock fitting which may be releasably engaged with a corresponding Luer lock fitting disposed within the first end of second hub 150*a*. The Luer lock fitting disposed on the second end of hub 140*a* may be in fluid communication with the bore or passage in cannula 110*a*, and may be operable to be releasably engaged with a standard syringe type fitting and/or a standard intravenous (IV) connection. In the embodiment shown, hub 150*a* includes second end 152 that generally corresponds with second end 132 of hub assembly 130*a* and second end 102 of IO needle set 100. Hub 140*a* may include first end 141 which may generally correspond with first end 131 of hub assembly 130*a*. Cannula 110*a* may extend longitudinally from first end 141 of hub 140*a* and first end 131 of hub assembly 130.

Figure 6A:
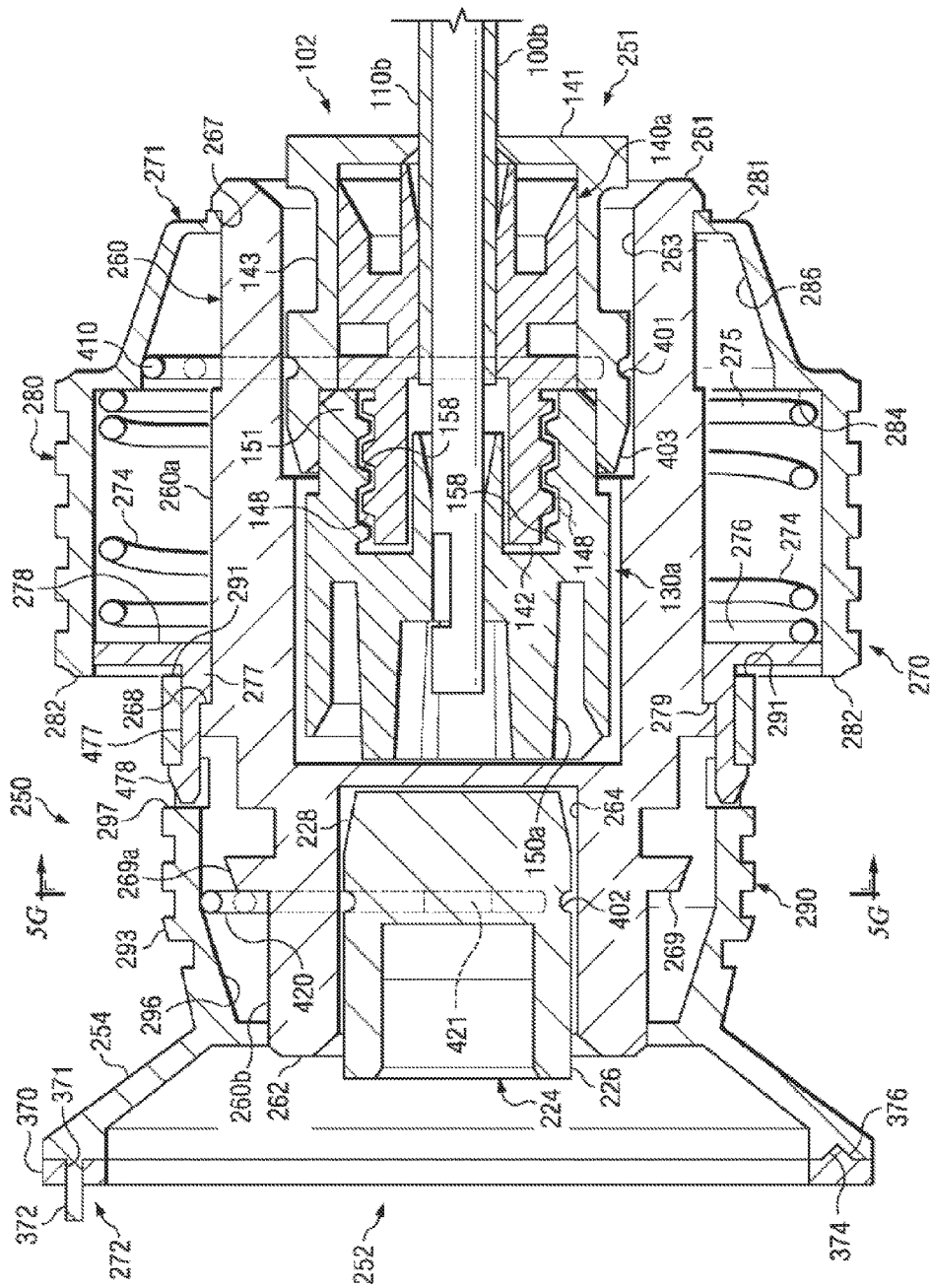
FIGS. 6A-6C depict various views of the coupler assembly of FIG. 3.
Figure 6B:
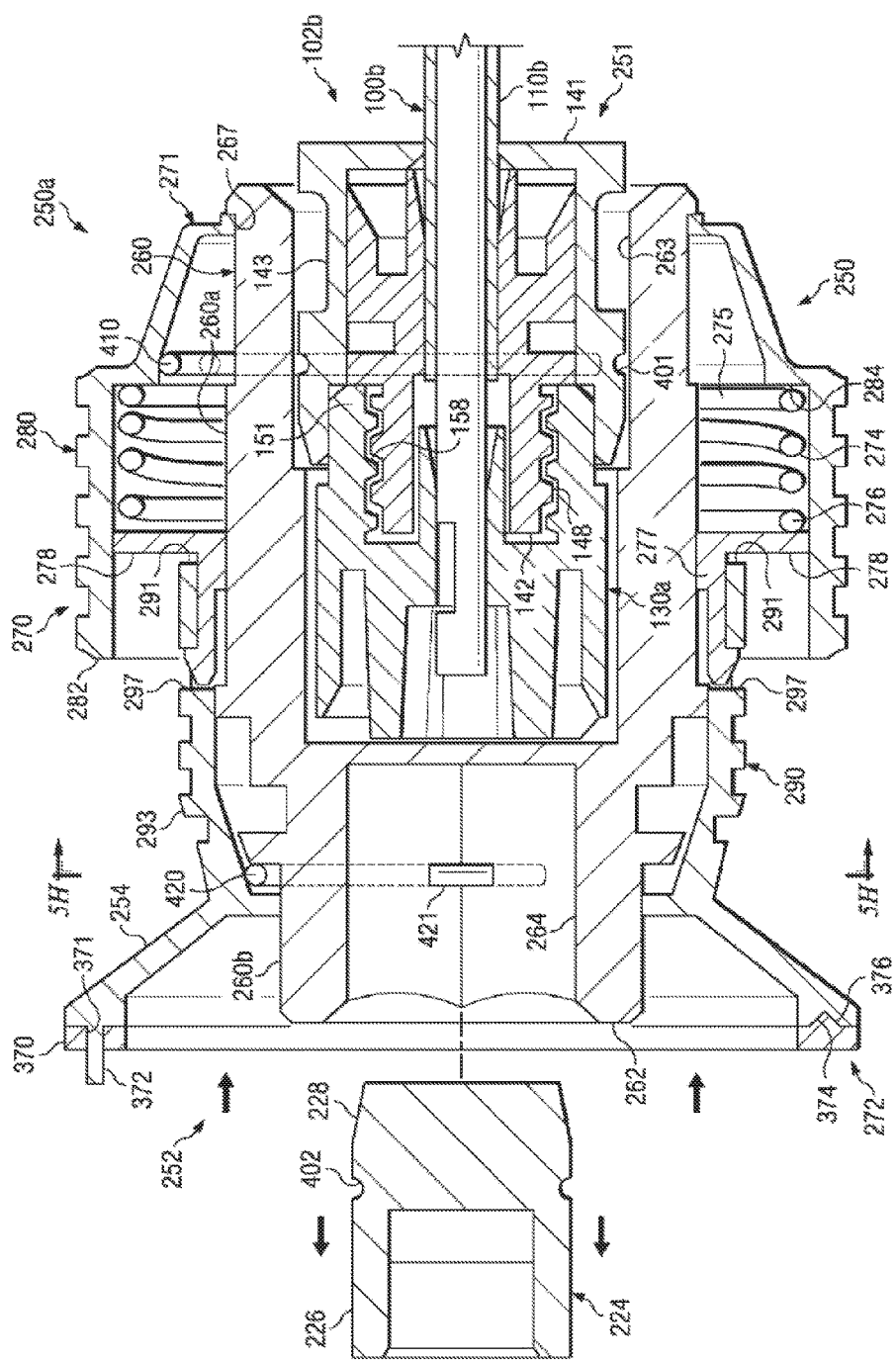

In the embodiment shown, the second end of a hub assembly may be operable to be disposed within a receptacle formed in a coupler assembly, as described in more detail below. One feature of the present disclosure may include forming a hub assembly which may be releasably engaged within a first receptacle disposed in a first end of a coupler assembly (e.g., receptacle 263 proximate first end 261 of elongated core 260 as shown in FIGS. 6A-6B). The dimensions and configuration of receptacle 263 may be selected to prevent rotation of hub 150*a* relative to hub 140*a* if hub assembly 130*a* is disposed in receptacle 263 (e.g., while inserting (rotating) an IO device into a bone and associated bone marrow). A powered driver may be releasably engaged with a second receptacle disposed in a second end of the coupler assembly (e.g., receptacle 264 proximate second end 262 of elongated core 260 as shown in FIGS. 6A-6B).

In the embodiment shown, intraosseous device or aspiration needle set 100*a* includes first end 151 of hub 150*a* spaced from second end 142 of hub 140*a*. Portions of stylet 120 extending from first end 151 of hub 150*a* are shown slidably disposed within lumen or longitudinal bore 118 of cannula 110*a*. Hub assembly 130*a* may include first end 131 which may correspond generally with first end 141 of hub 140*a*. Hub assembly 130*a* may also include second end 132 which may correspond generally with second end 152 of hub 150*a* and second end 102 of hub assembly 130*a*, as shown. Cannula 110*a* may be attached to and extend from first end 141 of hub 140*a*. Second end 142 of hub 140*a* may include one-half a typical Luer lock connection or fitting operable to be releasably engaged with corresponding portions of a Luer lock connection or fitting disposed in first end 151 of second hub 150*a*. For embodiments such as the one shown in FIG. 1A, first end 131 of hub assembly 130*a* may correspond with first end 141 of first hub 140*a*. Second end 152 of second hub 150*a* may correspond with second end 132 of hub assembly 130*a* and second end 102 of aspiration needle set 100*a*.

At least one portion of hub assembly 130*a* may have a generally hexagonal cross section operable to be received within the generally hexagonal cross section of receptacle 263 disposed proximate first end 251 of coupler assembly 250, as shown in FIGS. 6A-6B. For some embodiments, portions of first hub 140*a* disposed adjacent to reduced outside diameter portion 143 may have generally hexagonal cross sections, as shown in FIG. 1A. In other embodiments, various cross sections other than hexagonal may be satisfactorily used to releasably engage a powered driver with one end of a coupler assembly and an intraosseous device with an opposite end of the coupler assembly. Aspiration needle sets may include a stylet, stylet or penetrator in combination with an associated cannula, catheter or outer penetrator. However, biopsy needles formed in accordance with teachings of the present disclosure may or may not include a stylet, stylet or inner penetrator.

Hub 140*a* may include second end 142 with opening 144 formed therein. A passageway may extend from second end 142 towards first end 141 of hub 140*a*, as illustrated in FIGS. 6A-6B. A passageway may be operable to communicate fluids with lumen 118 of cannula 100*a*. Second end 142 of hub 140 may include various features of a conventional Luer lock connection or fitting, including threads 148, and corresponding threads 158 may be formed within first end 151 of hub 150*a*, as shown in FIGS. 6A-6B.

For some applications hub 140*a* and hub 150*a* may, for example, be formed using injection molding techniques. For such embodiments hub 140*a* may include reduced outside diameter portion 143 disposed between first end 141 and second end 142. In a similar manner a plurality of void spaces or cutouts 153 may be formed in hub 150*a* adjacent to and extending from second end 152 in the direction of first end 151. The configuration and dimensions of reduced diameter portion 143 and/or cutouts 153 may be varied to optimize associated injection in techniques and at the same time provide required configurations, dimensions and material strength to allow associated hub assembly 130*a* to function as described in this disclosure.

In some embodiments, tip 123 of stylet 120 may be disposed relatively close to a tip of cannula 110*a*. For some applications, first end 121 of stylet 120 and first end 111*a* of cannula 110*a* may be ground at the same time to form adjacent cutting surfaces. Grinding ends 111*a* and 121 at the same time may result in forming a single cutting unit to form generally matching cutting edges. Other types of cutting surfaces formed in accordance with teachings of the present disclosure may be discussed later (e.g., as described with reference to FIGS. 1B-1D).

Figure 1B:
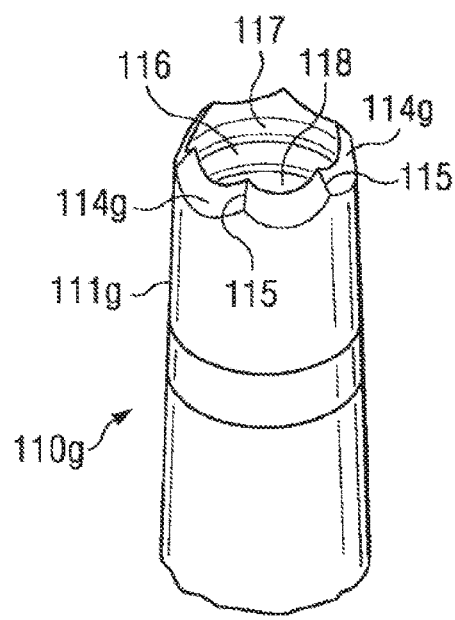
FIG. 1B depicts a perspective view of a portion of another prior art cannula.
Figure 1C:
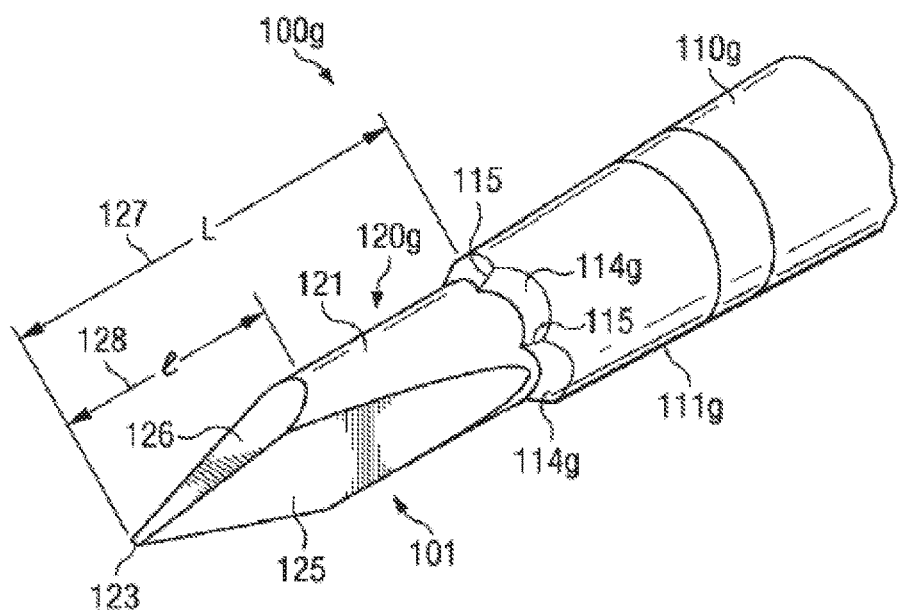
FIGS. 1C and 1D depict perspective views of a portion of a prior art IO device having a stylet disposed in the cannula of FIG. 1B.
Figure 1D:
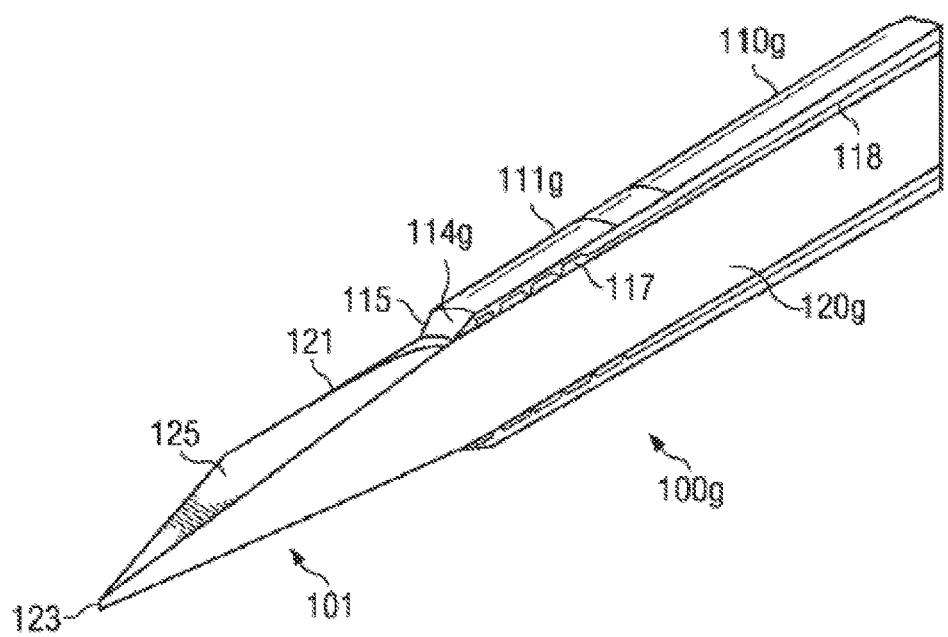
Figure 1E:
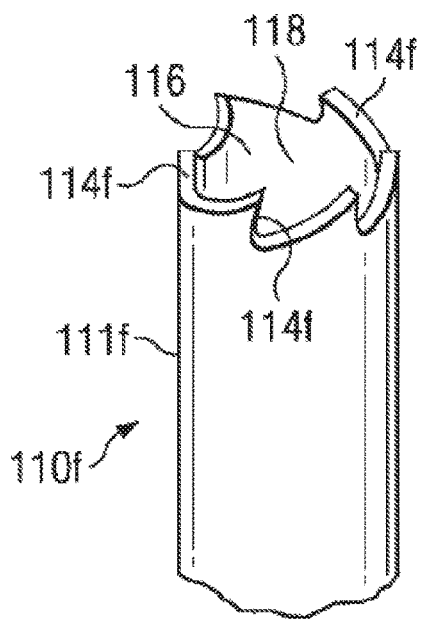
FIGS. 1E and 1F depict perspective views of portions of other prior art cannulas.
Figure 1F:
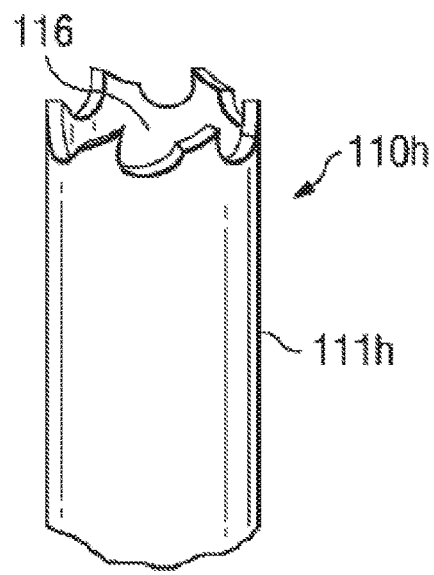

FIGS. 1B-1D show a second example of cutting surfaces and tips which may be formed adjacent to the ends of a cannula and/or an associated stylet in the present embodiments. In the embodiment shown, outer penetrator or cannula 110*g* may include first end 111*g* having a plurality of cutting surfaces 114*g* formed adjacent to opening 116 in first end 111*g*. Opening 116 may communicate with and form a portion of an associated longitudinal bore or lumen 118. For some applications cutting surfaces 114*g* may be formed using electrical discharge machining (EDM) techniques or otherwise, as described in WO 2008/033874. In the embodiment shown, first end 111*g* has a generally tapered configuration or reduced outside diameter as compared with other portions of cannula 110*g*. In other embodiments, first end 111*g* has an outside diameter that is equal to the outside diameter of other portions of cannula 110*g* (e.g., cannula 110*g* can have a constant outside diameter along the entire length of the cannula). Cutting surfaces 114*g* may, for example, be formed using machine grinding techniques. In some embodiments, such as the one shown, end 111*g* of cannula 110*g* may include six ground cutting surfaces 114*g* with respective crowns 115 therebetween. Forming a biopsy needle set and/or biopsy needle with tapered end 111*g* and a plurality of cutting surfaces 114*g* and crowns 115 may provide improved drilling performance (e.g., relative to others configurations) when the resulting biopsy needle set and/or biopsy needle is used with a powered driver in accordance with teachings of the present disclosure. For some applications, a helical groove 117 may be formed within longitudinal bore 118 proximate opening 116. Helical groove 117 may assist with retaining a biopsy specimen or a bone marrow specimen within longitudinal bore 118. For example, a single thread may be disposed within the longitudinal bore or lumen of the cannula such that the helical groove 117 is defined between turns of the thread. Various techniques and procedures may be satisfactorily used to place the single thread or otherwise form the helical groove, as described WO 2008/031874.

As shown in FIG. 1C, a biopsy needle set 100g may include cannula or outer penetrator 110g with stylet or inner penetrator 120g slidably disposed therein. The proximal ends of cannula 110g and stylet 120g may be similar to those of cannula 110a and stylet 120 depicted in FIG. 1A (e.g., may include hubs 140a and 150a, respectively). For some applications first end 101 of biopsy needle set 100g may minimize damage to skin and soft body tissue at an insertion site. For some applications inner penetrator or stylet 120g may include first end 121 having a plurality of cutting surfaces 125 and 126 formed on exterior portions thereof extending from associated tip 123 towards second end of stylet or inner penetrator 120g. For some applications one or more cutting surfaces 125 may be formed having length 127 extending from tip 123 to associated cutting surfaces 114g in associated cannula 110g. One or more cutting surfaces 126 may be formed adjacent to each cutting surface 125 with second length 128. First length 127 may be greater than second length 128. As shown, lengths 127 and 128 are measured parallel to the central longitudinal axis of stylet 120g. The ratio of first length 127 and second length 128 may be varied in accordance with teachings of the present disclosure to provide optimum performance for penetrating a selected bone and associated bone marrow. Additional details of some embodiments of first end 101 are described in WO 2008/033874.

Figure 2:
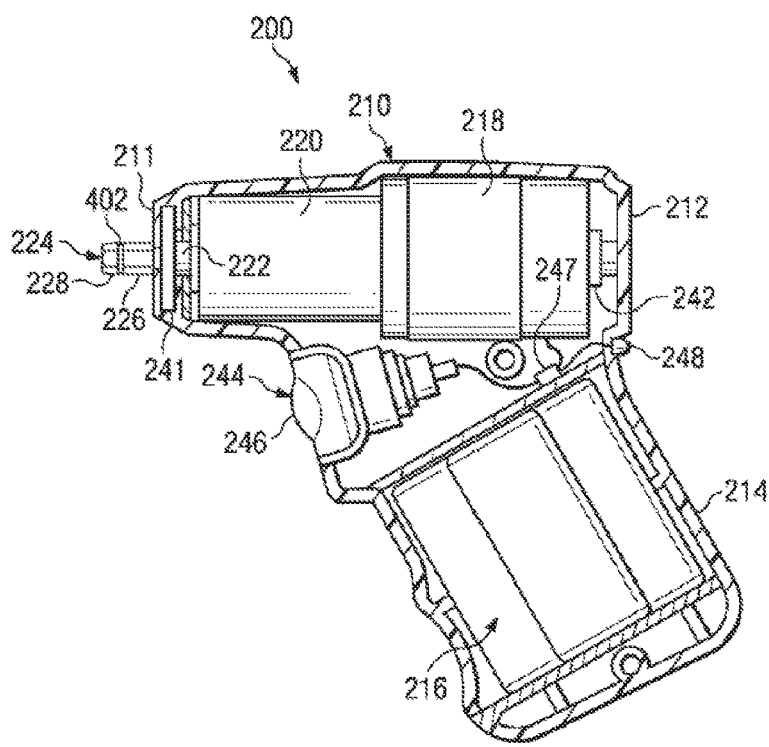
FIG. 2 depicts a cross-sectional side view of a prior art driver.

FIG. 2 depicts a cross-sectional view of one embodiment of a driver that can be used with embodiments of the present intraosseous needle sets and kits. In the embodiment shown, powered driver 200 may be used to insert one of the present intraosseous devices into a bone and associated bone marrow. Powered driver 200 may include housing 210 having a general configuration similar to a small pistol defined in part by handle 214. Various components associated with powered driver 200 may be disposed within housing 210 (e.g., handle 214). For example a power source such as battery pack 216 may be disposed within handle 214. Housing 210 may be formed from relatively strong, heavy duty polymeric materials such as polycarbonate or other satisfactory materials. For some applications housing 210 may be formed in two halves (not expressly shown) which may be joined together with a fluid tight seal to protect various components of powered driver 200 disposed therein.

Figure 6C:
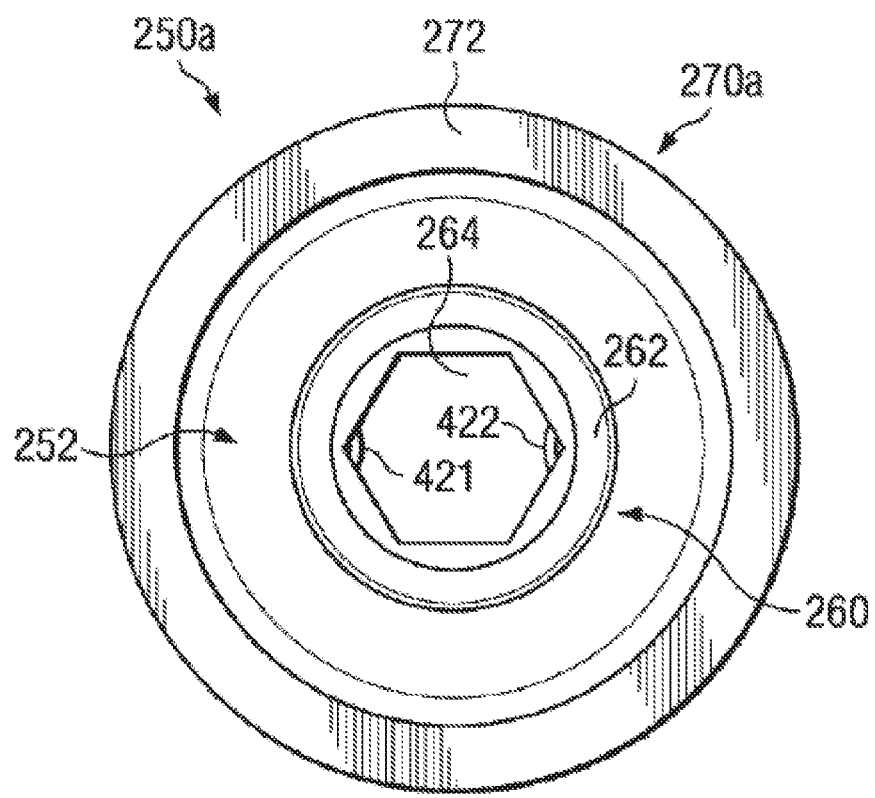

Motor 218 and gear assembly 220 may be disposed within portions of housing 210 adjacent to handle 214. Motor 218 and gear assembly 220 may be generally aligned with each other. Motor 218 may be rotatably engaged with one end of gear assembly 220. Drive shaft 222 may be rotatably engaged with and extend from another end of gear assembly 220 opposite from motor 218. For some applications both motor 218 and gear assembly 220 may have generally cylindrical configurations. Distal end or first end 211 of housing 210 may include an opening with portions of drive shaft 222 extending through the opening, as shown. For some applications, end 224 or the portion of drive shaft 222 extending from first end 211 of housing 210 may have a generally hexagonal cross section with surfaces 226 disposed thereon. Receptacle 263 disposed in second end 252 of coupler assembly 250 may have a matching generally hexagonal cross section, as shown in FIGS. 6A-6C.

Surfaces 226 may extend generally parallel with each other and parallel with respect to a longitudinal axis or rotational axis of drive shaft 222. One or more tapered surfaces 228 may also be formed on end 224 to assist with releasably engaging powered driver 200 with coupler assembly 250. Embodiments of powered driver 200 include speed reduction ratios, for example, of between 60:1 and 80:1, resulting in drive shaft RPMs that are reduced relative to motor RPMs. Coupler assemblies having corresponding openings or receptacles may be releasably engaged with end 224 extending from first end 211 of powered driver 200. For example, end 224 extending from first end 211 of housing 210 may be releasably engaged with receptacle 264 disposed proximate second end 252 of coupler assembly 250, as shown in FIGS. 6A-6B.

For some applications thrust bearing 241 may be disposed between first end or distal end 211 of housing 210 and adjacent portions of gear assembly 220. Thrust bearing 242 may be disposed between second end or proximal end 212 of housing 210 and adjacent portions of motor 218. Thrust bearings 241 and 242 may limit longitudinal movement of motor 218, gear assembly 220 and drive shaft 222 within associated portions of housing 210. Trigger assembly 244 may also be disposed within housing 210 proximate handle 214. Trigger assembly 244 may include trigger or contact switch 246. Motor 218 may be energized and deenergized by alternately depressing and releasing trigger 246. Electrical circuit board 247 may also be disposed within housing 210. Electrical circuit board 247 may be electrically coupled with trigger assembly 244, motor 218, power supply 216 and indicator light 248. For some applications indicator light 248 may be a light emitting diode (LED) or a small more conventional light bulb. For some applications indicator light 248 may be activated when ninety percent (90%) of electrical storage capacity of battery pack 216 has been used. The configuration and dimensions of an intraosseous device formed in accordance with teachings of the present disclosure may vary depending upon respective intended applications for each intraosseous device. For example the length of a biopsy needle formed in accordance with teachings of the present disclosure may vary from approximately five (5) millimeters to thirty (30) millimeters.

Coupler assemblies incorporating teachings of the present disclosure may function as "quick release mechanisms" operable to engage and disengage an device from a powered driver (e.g., a driver disposed within a flexible containment bag or sterile sleeve). Such coupler assemblies may allow rotation of an IO device (e.g., biopsy needle or needle set) without damage to the flexible containment bag or sterile sleeve. One end of the coupler assembly may be operable to form a fluid seal or fluid barrier with adjacent portions of the containment bag or sterile sleeve. A coupler assembly incorporating teachings of the present disclosure may also be described as a port assembly attached to a containment bag. Such port assemblies may allow easy engagement or disengagement of a powered driver from an IO device and at the same time allow the powered driver to "power in and power out" an IO device from an insertion site.

Figure 3:
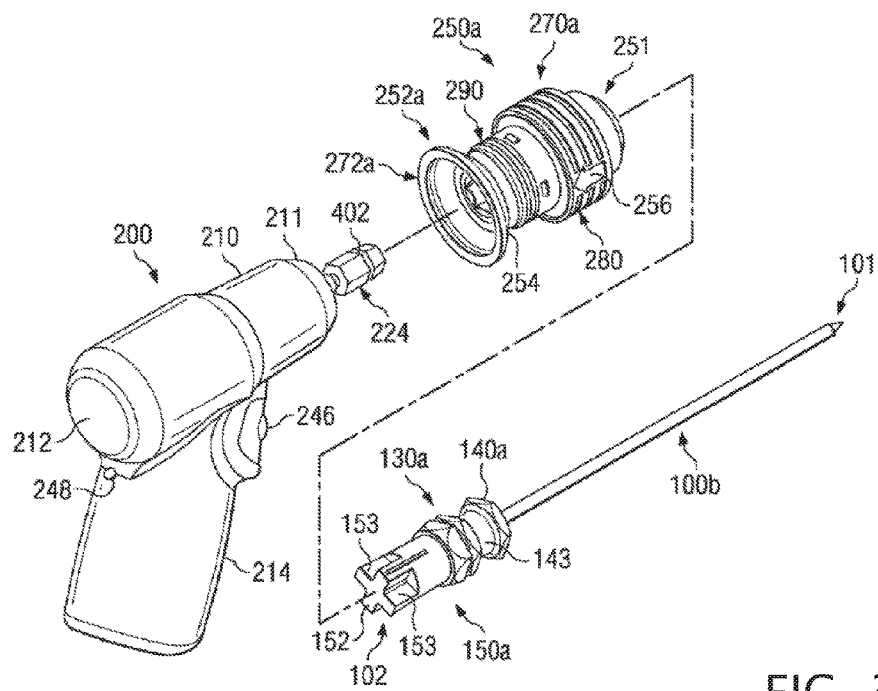
FIG. 3 depicts a perspective view of the driver of FIG. 2 with a prior art coupler assembly and a prior art IO device.
Figure 4:
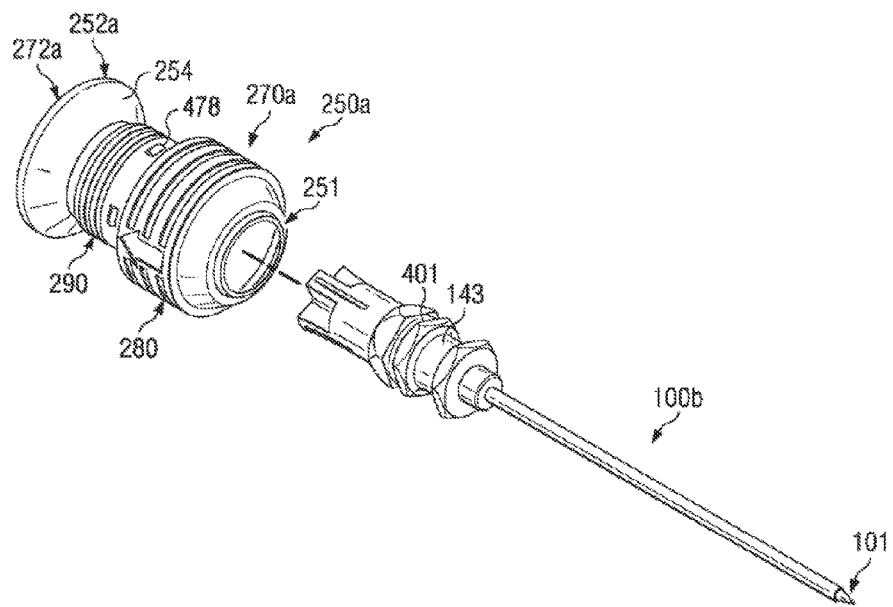
FIG. 4 depicts the coupler assembly and IO device of FIG. 3.
Figure 5:
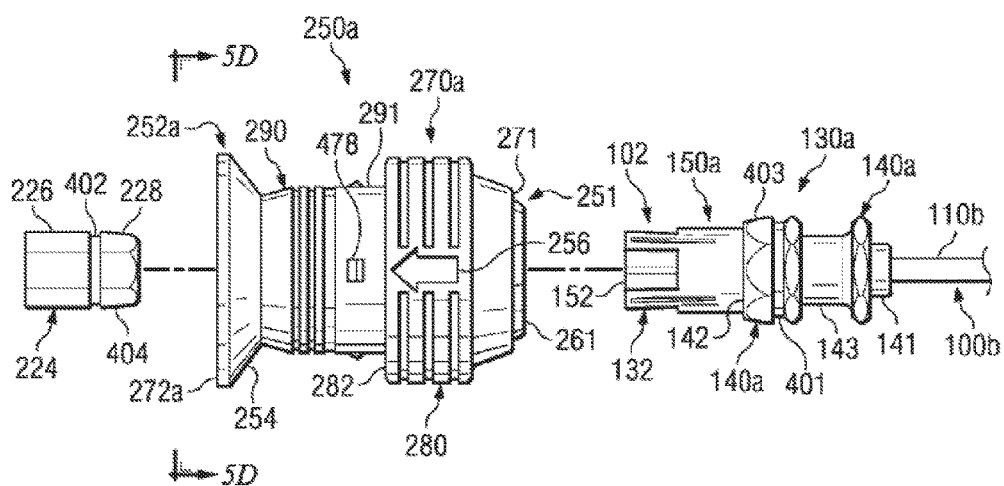
FIG. 5 depicts portions of the driver of FIG. 2 and the coupler assembly and a portion of the IO device of FIG. 3.

FIGS. 3-6C depict an example of a coupler assembly 250 suitable for some embodiments of the present assemblies and kits. FIGS. 3-5 are perspective views showing various views of powered driver 200, coupler assembly 250a, and intraosseous device 100b that is substantially similar to device 100a with the exception that device 100b does not include markings 104. Coupler assembly 250a includes a first end 251 operable to be releasably engaged with one end of an intraosseous device such as, but not limited to, second end 102 of biopsy needle set 100b. Coupler assembly 250a also includes a second end 252 operable to be releasably engaged with a portion of a drive shaft extending from a powered driver, such as, but not limited to, end 224 of drive shaft 222 extending from first end 211 of housing 210 of powered driver 200. Though not depicted here, second end 252 of coupler assembly 250 may be securely engaged with an opening in a containment bag or sterile sleeve, as described in WO 2008/033874.

Coupler assemblies incorporating various teachings of the present disclosure may be placed in a medical procedure tray or kit with one end down and an opposite end looking up to allow "hands free" releasable engagement with a powered driver or a manual driver. For example, coupler assembly 250a may be disposed in medical procedure tray with first end 251 facing downward and second end 252 facing up such that end 224 of drive shaft 222 (of driver 200) may be inserted into and releasably engaged with second end 252 of coupler assembly 250 without requiring an operator or user to physically contact or manipulate any portion of coupler assembly 250a. As described below, coupler 250a may include a "hands free" latching mechanism.

In the embodiment shown, coupler assembly 250a may include elongated core 260 with housing assembly 270 slidably disposed on exterior portions of elongated core 260. Housing assembly 270/270a may include first end 271 and second end 272 which may be generally aligned with respective first end 261 and respective second end 262 of elongated core 260. For some applications, elongated core 260 may have a generally cylindrical configuration defined in first exterior portion 260a and second exterior portion 260b with various shoulders and/or recesses formed thereon. For some embodiments first exterior portion 260a may have a larger diameter than second exterior portion 260b. Housing assembly 270 may be described as having a generally hollow, cylindrical configuration defined in part by first housing segment 280 and second housing segment 290. The first end of housing segment 280 may generally correspond with first end 271 of housing assembly 270. The second end of second housing segment 290 may generally correspond with second end 272 of housing assembly 270. First end 291 of second housing segment 290 may be described as having a generally cylindrical configuration with an outside diameter smaller than the adjacent inside diameter of second end 282 of first housing segment 280. Second housing segment 290 may slide longitudinally from a first position (FIG. 6A) to a second position (FIG. 6B) within second end 282 of first housing segment 280 to release one end of a drive shaft engaged with second end 252 of coupler assembly 250.

A biasing mechanism such as coiled spring 274 may be disposed around exterior portion 260a of generally elongated core 260. First end 275 of coiled spring 274 may contact annular shoulder 284 formed on interior portions of first housing segment 280. Second end 276 of coiled spring 274 may contact annular shoulder 278 disposed proximate first end 291 of second housing segment 290. Coil spring 274, annular shoulder 284 and annular shoulder 278 may cooperate with each other to generally maintain first housing segment 280 and second housing segment 290 in a first extended position relative to each other. Other biasing mechanisms such as, but not limited to, leaf springs and bellows (not expressly shown) may also be disposed between annular shoulder 284 and annular shoulder 278.

Annular shoulder 278, associated with second end 276 of coiled spring 274, may extend radially outward from generally cylindrical ring 277. Generally cylindrical ring 277 may be slidably and rotatably disposed on exterior portion 260a of elongated core 260. Annular shoulder 279 may be disposed on interior portions of generally cylindrical ring 277 and may extend radially inward toward adjacent portions of elongated core 260. Annular shoulder 268 may be formed on exterior portion 260a of elongated core 260 intermediate first end 261 and second end 262. The configuration and dimensions of annular shoulder 268 and annular shoulder 279 are selected to be compatible with each other such that engagement between annular shoulder 279 of generally cylindrical ring 277 with annular shoulder 268 of elongated core 260 may limit movement of second housing segment 290 longitudinally in the direction of second end 262 of elongated core 260.

For some applications a plurality of flexible collets or fingers 477 may extend from generally cylindrical ring 277 opposite from annular shoulder 278. Respective collet heads 478 may be formed on the end of each collet 477 opposite from annular shoulder 278. The dimensions and configuration of collet heads 478 may be selected to be received within respective slots or openings 297 formed in second housing 290. During manufacture of coupler assembly 250a, each collet head 478 may be disposed within respective slot or opening 297 to securely engage generally cylindrical ring 277 and annular shoulder 278 proximate first end 291 of second housing segment 290. As a result, second housing segment 290 and annular shoulder 278 may generally move as a single unit relative to elongated core 260 and first housing segment 280. During disengagement of an intraosseous device from first end 251 of coupler assembly 250a, first housing segment 280 may move or slide longitudinally toward second housing segment 290. In a similar manner, second housing segment 290 may move or slide longitudinally toward first housing segment 280 during disengagement of a powered driver from second end 252 of coupler assembly 250a.

Annular shoulder 267 may be formed on exterior portions of elongated core 260 proximate first end 261. Annular shoulder 267 may engage portions of first end 271 of housing 270 to limit longitudinal movement of first housing segment 280 during longitudinal movement of second housing segment 290 towards first end 261 of elongated core 260 during disengagement of a powered driver from second end 252 of coupler assembly 250a. As previously noted annular shoulder 268 may be formed on exterior portions of elongated core 260 between first end 261 and second end 262. Engagement between annular shoulder 268 and annular shoulder 279 of generally cylindrical ring 277 may limit movement of second housing segment 290 toward second end 262 of elongated core 260. Contact between spring 274 and annular shoulder 278 and annular shoulder 284 of first housing segment 280 may limit the longitudinal movement of first housing segment 280 in the direction of second end 262 of elongated core 260 during disengagement of an intraosseous device from first end 251 of coupler assembly 250a.

Generally cylindrical ring 277 and attached annular shoulder 279 may slide longitudinally on exterior portions of annular core 260 between annual shoulder 268 and annular shoulder 267. First housing segment 280 may move longitudinally toward second end 262 of elongated core 260 to release one end of intraosseous device from engagement with first end 251 of coupler assembly 250a. In a similar manner, second housing segment 290 may move longitudinally toward first end 261 of elongated core 260 to release one end of a drive shaft extending from a powered driver engaged with second end 252 of coupler assembly 250a. A wide variety of latches and latch mechanisms may be satisfactorily used to releasably engage one end of an intraosseous device within a first end of a coupler assembly incorporating teachings of the present disclosure. In a similar manner, a wide variety of latches and latch mechanisms may be satisfactorily used to releasably engage one end of a drive shaft extending from a powered driver or manual driver within a second end of the coupler assembly incorporating teachings of the present disclosure.

For embodiments represented by coupler assembly 250a, first latch 410 may be disposed on exterior portions of elongated core 260 proximate receptacle 263 adjacent to first end 261 to releasably engage one end of an IO device such as second end 102 of biopsy needle set 100b within receptacle 263 of coupler assembly 250a. Second latch mechanism 420 may be disposed on exterior portions of elongated core 260 proximate receptacle 264 adjacent to second end 262 to releasably engage one end of a drive shaft with second end 252 of coupler assembly 250a. Second latch 420 may be used to releasably engage one portion of a drive shaft such as end 224 of drive shaft 222 extending from powered driver 200 within second end 252 of coupler assembly 250a. Latch 410 may releasably engage an intraosseous device with first end 251 of coupler assembly 250a and substantially the same latch 420 may releasably engage a powered driver with second end 252 of coupler assembly 250a.

For some applications, latches 410 and 420 may have similar configurations such as a general "omega" shape (e.g., latch 420). However, latch 410 may have larger dimensions corresponding generally with exterior portion 260a of elongated core 260. Latch 420 may have smaller dimensions corresponding generally with exterior portion 260b of elongated core 260. Various features of the present disclosure may be described with respect to latch mechanism 420 along with adjacent portions of second housing segment 290 and exterior portion 260b of elongated core 260. Respective detents 421 and 422 may be formed on opposite ends of generally omega shaped latch 420. In a similar manner, respective detents (not expressly shown) may be formed on the ends of generally omega shaped latch 410. The configuration and dimensions of detents 421 and 422 may be compatible with placing each detent 421 and 422 in a respective slot or opening extending between exterior portion 260b of elongated core 260 to interior portions of receptacle 264 disposed proximate second end 252 of coupler assembly 250a. Latch 420 may have a first position in which portions of detents 421 and 422 may extend through the respective slots. The dimensions and configuration of detent 421 and 422 may be operable to be securely engaged with annular groove 402 formed in end 224 of powered driver 200. In a similar manner, respective detents on associated latch 410 may be releasably engaged with annular groove 401 disposed in second end 102 of biopsy needle 100b. For some applications, a plurality of tapered surfaces 403 may be formed on exterior portions of hub 140a proximate first end 142 to radially expand detent mechanisms associated with omega shaped latch 410 radially outward while inserting second end 102 of biopsy needle 100b into first end 251 of coupler assembly 250a. The detent mechanism may snap into annular groove 401 when aligned therewith. In a similar manner, a plurality of tapered surfaces 228 may be formed on exterior portions of end 224 of drive shaft 222 extending from powered driver 200 to radially expand detent mechanisms 421 and 422 radially outward during the insertion of end 224 of powered driver 200 into second end 252 of coupler assembly 250a. Detent mechanisms 421 and 422 will "snap" into annular groove 402 when aligned therewith.

Engagement between detent mechanisms associated with latch 410 with annular groove 401 of hub assembly 130a will generally retain second end 102 of biopsy needle 100b securely engaged with first end 251 of coupler assembly 250a. This engagement may allow powered driver 200 to rotate or spin cannula or biopsy needle 110b while withdrawing cannula or biopsy needle 110b from an insertion site. In a similar manner, engagement between detent mechanisms 421 and 422 of omega shaped latch 420 and annular groove 402 of end 224 of powered driver 200 will generally retain second end 252 of coupler assembly 250a engaged with powered driver 100 during withdrawal of cannula 110b from an insertion site.

Biopsy needle set 100b may be released from first end 251 of coupler assembly 250a by sliding first housing segment 280 longitudinally toward second end 262 of elongated core 260. Such movement of first housing segment 280 will result in interior tapered surface 286 contacting exterior portions of omega shaped latch 410 and compressing omega shaped latch 410 to radially expand associated detent mechanisms (not expressly shown) from engagement with annular groove 401 of hub assembly 130a. As a result, biopsy needle set 100b may be easily withdrawn from first end 251 of coupler assembly 250a. In a similar manner, longitudinal movement of second housing segment 290 toward first end 251 of coupler assembly 250a will result in interior tapered surface 296 contacting exterior portions of omega shaped latch 420 to compress generally omega shaped latch 420 and withdraw or retract detent mechanisms 421 and 422 from engagement with annular groove 402 of end 224. As a result, powered driver 200 and second end 222 of coupler assembly 250a may be easily disconnected from each other.

Flange 254 may be generally described as having an enlarged funnel shaped or bell shaped configuration. The dimensions and configuration of flange 254 may be selected to be compatible with end 211 of powered driver 200. As previously noted, coupler assembly 250a may be securely engaged with an opening formed in a containment bag or sterile sleeve in accordance with teachings of the present disclosure. For embodiments such as the one shown, end 272 of housing 270 of coupler assembly 250a may include annular ring 370 operable to be securely engaged with adjacent portions of flange 254. The outside diameter of annular ring 370 may generally correspond with the outside diameter of adjacent portions of flange 254. The inside diameter of annular ring 370 may also generally correspond with the inside diameter of adjacent portions of flange 254. For some embodiments a plurality of posts 372 and generally V shaped grooves 374 may be alternatingly disposed on the extreme end of flange 254. Annular ring 370 may include a plurality of holes 371 sized to received respective posts 372 therein. Annular ring 370 may also include a plurality of generally V shaped projections 376 sized to be received within respective generally V shaped grooves 374 formed in adjacent portions of flange 254. For embodiments such as the one shown, portions of a containment bag (e.g., around an opening) may be disposed between annular ring 370 and adjacent portions of flange 254. For example, post 372 may be inserted through a corresponding hole in a containment bag adjacent to the perimeter of an opening in the containment bag. Holes 371 in annular ring 370 may be aligned with respective posts 372. Other portions of a containment bag (e.g., adjacent to an opening) may be trapped between respective V shaped projections 376 and V shaped grooves 374. Various welding techniques including, but not limited to, laser welding may be applied to posts 372 to bond annular ring 370 with adjacent portions of flange 354. As a result, a perimeter of a containment bag around an opening in the containment bag may be securely engaged with second end 252 of coupler assembly 250*a*.

Figure 7A:
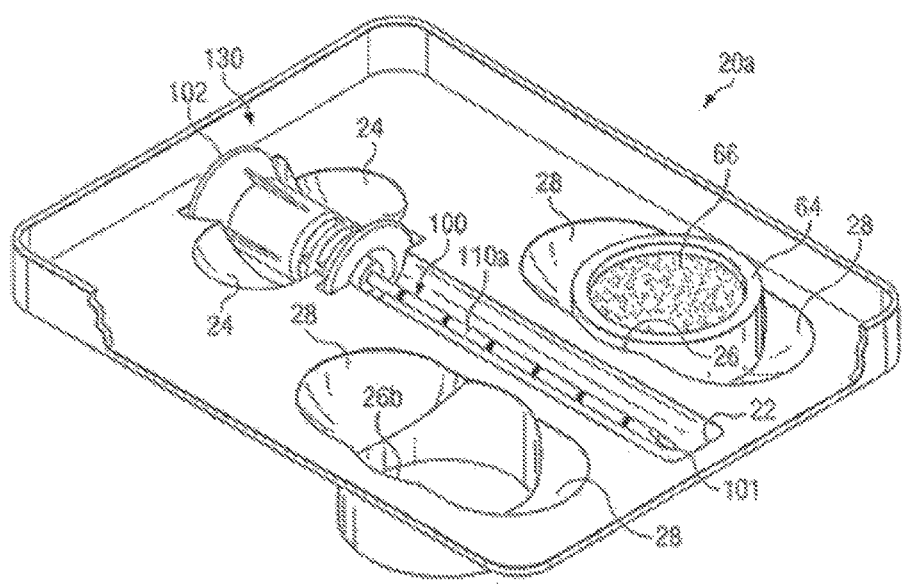
FIGS. 7A-7C depict various views of prior art kits.
Figure 7B:
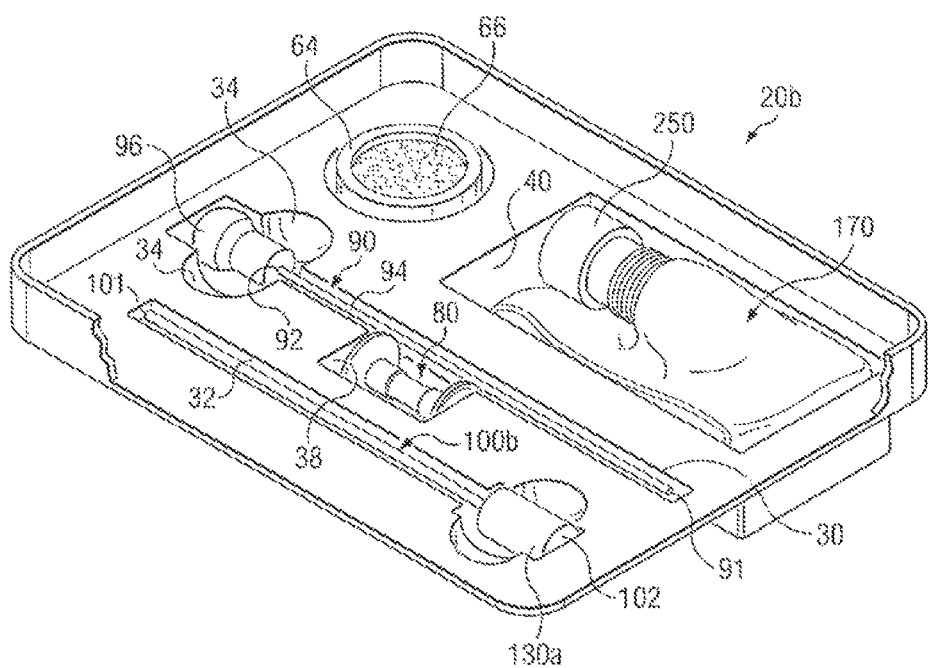
Figure 7C:
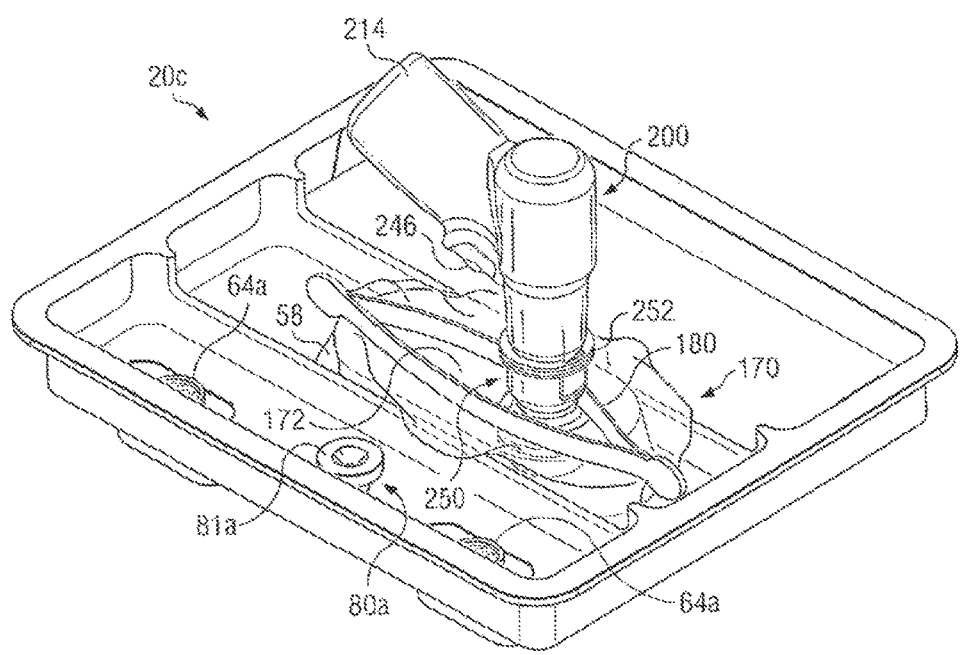
Figure 8:
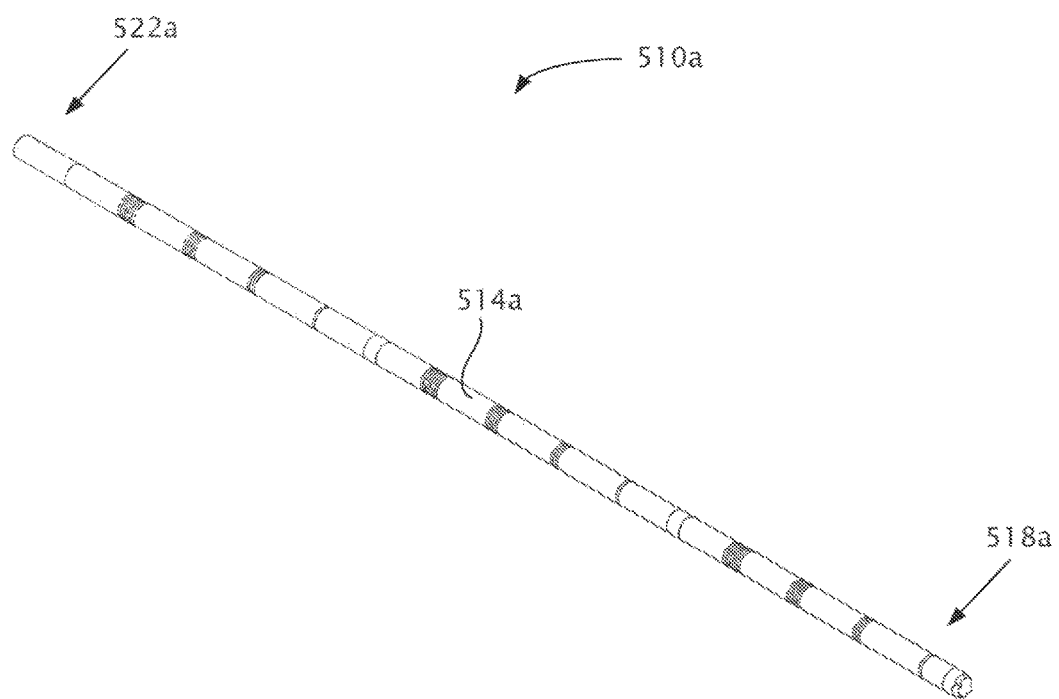
FIG. 8 depicts a perspective view of one embodiment of a cannula of the present intraosseous needle sets.
Figure 9A:
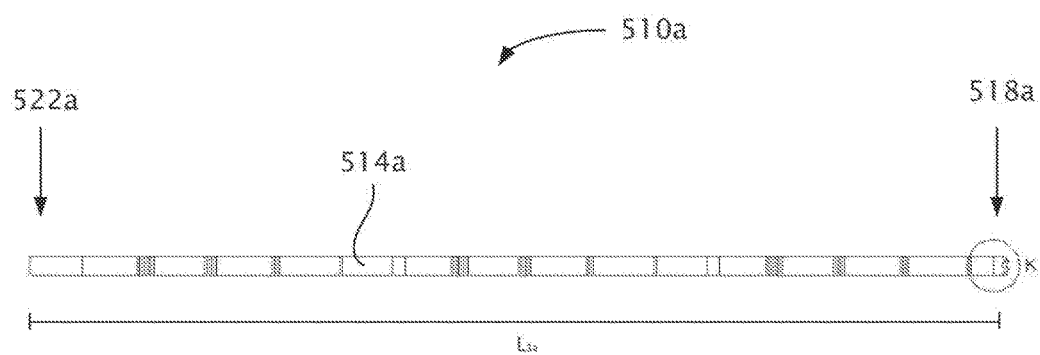
FIG. 9A depicts a side view of a cannula having a bore that is substantially circular.
Figure 9B:
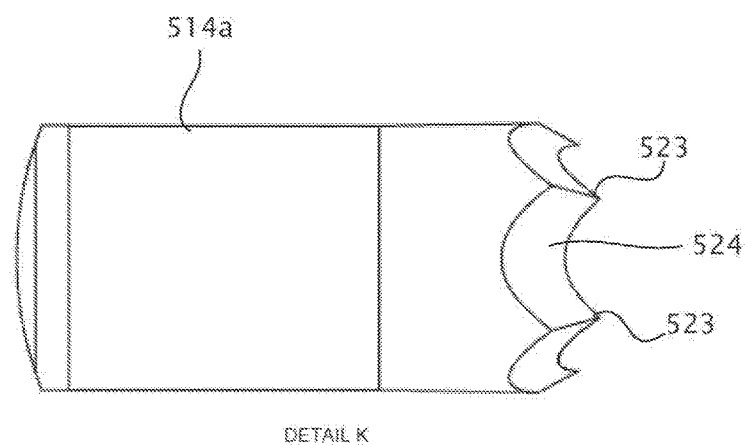
FIG. 9B depicts a side view of a portion of the cannula of FIG. 9A.

FIGS. 7A-7C show some examples of medical procedure trays and/or kits which may contain one or more intraosseous devices and/or other components incorporating teachings of the present disclosure. For example, medical procedure tray 20*a* as shown in FIG. 7A may include intraosseous needle set or aspiration needle set 100 incorporating various teachings of the present disclosure. Medical procedure tray 20*b* as shown in FIG. 7B may include intraosseous needle set or biopsy needle set 100*b*, ejector 90, funnel 80 and/or containment bag or sterile sleeve 170. Medical procedure tray 20*c* as shown in FIG. 7C may also include various IO devices and other components incorporating teachings of the present disclosure including, but not limited to, biopsy needle set 100*b*, coupler assembly 250, containment bag 170, ejector 90 and/or funnel 80*a*.

Medical procedure trays and/or kits formed in accordance with teachings of the present disclosure may provide a support or base for various components such as a coupler assembly, funnel, and/or sharps protector to allow an operator or user to perform various functions without requiring that the operator or user hold or manipulate the respective component. For example, medical procedure tray 20*c* as shown in FIG. 7C may position and support coupler assembly 250 such that one end of a powered driver may be inserted (pushed) into releasable engagement with second end 252 of coupler assembly 250. The powered driver may then be used to withdraw coupler assembly 250 from medical procedure tray 20*c* without requiring an operator or user to directly hold or manipulate coupler assembly 250.

Medical procedure trays 20*a*, 20*b* and/or 20*c* may also contain a wide variety of other components including, but not limited to, one or more sharps protectors 64 as shown in FIGS. 7A and 7B. Sharps protectors 64 may include hard foam or claylike material 66 disposed therein. Intraosseous devices such as aspiration needle sets and biopsy needle sets typically have respective sharp tips and/or cutting surfaces operable to penetrate skin, soft tissue and bone. The sharp tips and/or cutting surfaces of such intraosseous devices may be inserted into hard foam or claylike material 66 after completion of a medical procedure using the respective intraosseous device.

FIG. 7C shows one procedure for placing a powered driver within a containment bag incorporating teachings of the present disclosure. Containment bag 170 may be formed from generally flexible, fluid impervious material which may also be sterilized using conventional sterilization techniques. Containment bag 170 may be used to prevent a non-sterile powered driver from contaminating a sterile intraosseous device and/or an injection site, particularly during a bone marrow biopsy procedure or a bone marrow aspiration procedure. Containment bag 170 may be operable to form a fluid barrier with adjacent portions of housing assembly 270. At the same time, coupler assembly 250 may allow powered driver to rotate an intraosseous device releasably engaged with first end 251 of coupler assembly 250 without damage to containment bag 170.

Referring now to FIGS. 8-14C, designated by reference numerals 510*a* and 510*b* are embodiments of the present intraosseous needle sets. In the embodiments shown, intraosseous needle sets 510*a* and 510*b* (referred to collectively as intraosseous needle sets 510) are configured to penetrate a target area (e.g., independently and/or in combination with other intraosseous devices, drivers, couplers, and the like). In the embodiments shown, intraosseous needle sets 510 comprise cannulas 514*a* and 514*b* (referred to collectively as cannulas 514) having first ends 518*a* and 518*b* (referred to collectively as first ends 518) and second ends 522*a* and 522*b* (referred to collectively as second ends 522). First ends 518 and second ends 522 of cannulas 514 can be configured similarly to first and second ends of cannulas depicted in FIGS. 1A and 3-6B and previously described in this disclosure. First ends 518 and second ends 522 can also be configured as described below.

Cannulas 514 comprise lengths L1a and L1b (referred to collectively as lengths L1) extending from first ends 518 to second ends 522. For example, in some embodiments, lengths L1 can be 3 inches to 12 inches (e.g., 6 inches); and in other embodiments, lengths L1 can be less than 3 inches or greater than 12 inches (e.g., depending on the physical orientation or location of a target area, a corresponding intraosseous device, a given procedure, and the like).

In the embodiments shown, first ends 518 of cannulas 514 can comprise at least one cutting surface (e.g., one, two, or more cutting surfaces) configured to penetrate a target area. For example, in the embodiment shown in FIGS. 8-10C, first end 518*a* of cannula 514*a* comprises plurality of crowns 523 having at least one cutting surface 524 between adjacent crowns. As another example, in the embodiment shown in FIGS. 11-14C, first end 518*b* of cannula 514*b* comprises plurality of teeth 526 each having tip 527. Tip 527 of teeth 526 can be disposed at angle B, where angle B can be 0 to 15 degrees, 15 to 30 degrees, and the like. In the embodiment shown in FIGS. 11-14C, each of plurality of teeth 526 comprises first side 528 and second side 529. For example, in the embodiment shown, first side 528 has a length that is less than a length of second side 529. Tip 527 can be defined by an intersection of first side 528 and second side 529. Further, first side 528 of a first tooth can intersect with second side 529 of an adjacent second tooth to define angle A (e.g., 55 to 80 degrees).

In the embodiments shown, cannulas 514 further comprise bores 534*a* and 534*b* (referred to collectively as bores 534). Bores 534 can be configured to accommodate intraosseous devices (e.g., such as a stylet, discussed further below) such that the intraosseous devices and cannulas 514 cooperate to penetrate a target area. Bores 534 can further be configured to receive a sample from a target area (e.g., if cannulas 514 rotate into a target area).

In the embodiments shown, bores 534 comprise lengths L2a and L2b (referred to collectively as lengths L2 and not depicted) extending from second ends of bores 534 (corresponding to second ends of cannulas 514) through first ends of bores 534 (corresponding to first ends 518 of cannulas 514). Lengths L2 of bores 534 can be substantially equal to lengths L1 of cannulas 514 and can also be a different length (e.g., depending on whether bores 534 extend through second ends of cannulas 514).

In the embodiments shown, bores 534 comprise a circular cross-section with a substantially constant diameter along a majority of lengths L2. For example, a circular cross-section can extend 50% to 99% of lengths L2. In some embodiments, bores 534 can comprise a circular cross-section that extends greater than 99% of lengths L2 of bores 534 (e.g., depending on a desired sample size, a physical orientation of a target area, a corresponding intraosseous device, etc.). In the embodiments shown, bores 534 further comprise a non-circular cross-section (e.g., defined by first ends 518 of bores 534, as depicted in FIGS. 10C and 14C) along a minority of lengths L2 of bores 534. For example, a non-circular cross-section can extend 1% to 50% of lengths L2 of bores 534 (e.g., 0.1 to 0.5 inches of lengths L2 of bores 534). In some embodiments, a non-circular cross section can extend less than 1% or greater than 50% of lengths L2 of bores 534 (e.g., depending on a desired sample size, a physical orientation of a target area, a corresponding intraosseous device, etc.). In still other embodiments, a non-circular cross-section can extend a majority of lengths L2 (e.g., such that the circular cross-section of bores 534 extends a minority of lengths L2 of bores 534).

In the embodiments shown, the non-circular cross section is closer to first ends 538 of bores 534 than to second ends of bores 534. For example, a non-circular cross-section can begin at and/or extend from first ends 538 of bores 534 toward second ends 522 of bores 534. In the embodiments shown, a non-circular cross-section of bores 534 can have a first transverse dimension represented by distances D1a and D1b (referred to collectively as D1). The non-circular cross-section of bores 534 can also have a second transverse dimension represented by D2a and D2b (referred to collectively as D2). As depicted in FIGS. 10C and 14C, a first transverse dimension (e.g., D1) of bores 534 can be greater than a second transverse dimension (e.g., D2) such that bores 534 comprise a substantially non-circular cross-section. D2 can comprise, for example, 94-97% the length of D1. In other embodiments, D2 can comprise less than 94% (e.g., 80% to 94%, or less) or greater than 97% (e.g., 97% to 99%, or more) the length of D1 (e.g., depending on a desired sample size, a physical orientation of a target area a configuration of an intraosseous device disposed within bores 534, etc.). At a circular cross-section of bores 534, first and second transverse dimensions of bores 534 comprise substantially the same length (e.g., D1 and D2 are substantially equal).

Intraosseous needle sets 510 can be configured to receive a sample from a target area. The shape of the received sample can depend on a given configuration of bores 534 and/or first ends 518 of cannulas 514. For example, a user can penetrate a target area with cannulas 514 having bores 534 with a first traverse dimension (e.g., D1) and a second traverse dimension (e.g., D2) such that the sample comprises a circular cross-section with a substantially constant diameter substantially equal to the second traverse dimension (e.g., the smaller of the two traverse dimensions (e.g., D2 in the embodiment shown)). In this example, the circular cross-section of the sample is smaller than the circular cross-section of bores 534 (e.g., assisting a user in evacuating the sample). In other embodiments, bores 534 can have a plurality (e.g., 3, 4, 5, 6, 7, or more) of transverse dimensions. A sample received in such an embodiment can comprise, for example, a substantially constant diameter substantially equal to the smallest of the plurality of transverse dimensions.

In the embodiments shown in FIGS. 8-14C, intraosseous needle sets 510 can comprise a stylet (or trocar) configured to be disposed in bores 534 of cannulas 514. A stylet can be configured to cooperate with first ends 518 of cannulas 514 to define a tip for penetrating a target area (e.g., as shown in FIG. 1C). In some embodiments, a tip formed by cannulas 514 and a stylet can be substantially planar. In some embodiments, a first end of a stylet can have at least one tip, at least one first tapered cutting surface extending a first length from the tip, and at least one second tapered cutting surface extending a second length from the tip (e.g., as depicted in FIG. 1C). In some embodiments, the length of the first tapered cutting surface is less than the length of the second tapered cutting surface. In still other embodiments, a first end of a stylet can comprise a surface (e.g., a blunted surface) configured to evacuate a sample received from a target area from bores 534 of cannulas 514.

Intraosseous needle sets 510 can further comprise one or more components and/or characteristics of any of the other intraosseous needle sets and/or devices described in this disclosure. For example, in some embodiments, intraosseous needle sets 510 can comprise a first hub configured to be coupled to cannulas 514. The first hub can be similar to first hubs described and depicted throughout this disclosure (e.g., FIGS. 1A, 3-6B). For example, the first hub can comprise a second end and a first end coupled (e.g., securely or removably) to a second end of a cannula (e.g., second ends 522 of cannulas 514). In some embodiments, the first hub can be configured to limit the depth to which a cannula can penetrate a target area (e.g., via a depth limiter, as depicted in FIG. 1A). In some embodiments, the second end of the first hub can be configured to be coupled to a variety of intraosseous devices, such as, for example, a fluid bag (e.g., an IV fluid bag, etc.), an aspiration device, and the like. The second end of the first hub can comprise various coupling configurations depending on the intraosseous device, coupler, and/or hub to which the first hub is coupled, if any.

Intraosseous needle sets 510 can further comprise a second hub configured to be coupled (e.g., securely or removably) to a stylet (e.g., as shown in FIG. 1A). The second hub can be configured to be coupled to a first hub (e.g., while the first hub is coupled to a cannula (e.g., cannulas 514)) such that a stylet and the cannula can rotate in fixed relation to one another. The second hub can be configured to be coupled to the first hub, for example, by threads, a Luer lock fitting, and the like (e.g., as shown in the embodiment in FIG. 1A). The second hub can also comprise various coupling configurations depending on the intraosseous device, coupler, and/or hub to which the second hub is be coupled, if any.

As with other embodiments of intraosseous devices described and depicted throughout this disclosure, intraosseous needle sets 510 can be coupled to a manual and/or a powered driver. A manual driver can comprise a handle and a drive shaft configured to be coupled (e.g., removably) to a cannula (e.g., cannulas 514) and/or a stylet. Further, intraosseous needle sets 510 can be coupled to a powered driver (e.g., as in FIG. 3). The powered driver can comprise, for example, a housing having a handle, a drive shaft, a motor coupled to the drive shaft, a power source (e.g., a battery) coupled to the motor, and/or a trigger coupled to the motor and configured to activate the motor. The drive shaft can be configured to be coupled to at least one of a coupler (e.g., as in FIG. 3), a cannula (e.g., cannulas 514), and/or a stylet. The motor can be configured to rotate and/or move a drive shaft such that at least one of a stylet, a cannula (e.g., cannulas 514), and/or other intraosseous devices can penetrate a target area.

Intraosseous needle sets 510 can further be coupled to a coupler (e.g., such as a coupler assembly described in this disclosure and depicted in, for example, FIGS. 6A-6B). A coupler can be configured to couple a driver (e.g., manual or powered) to at least one of a cannula (e.g., cannulas 514), a stylet, a first hub, and a second hub.

Embodiments of intraosseous needle sets 510 (or components thereof) can further be included in one or more kits. In some embodiments, a kit containing intraosseous needle sets 510 (or components thereof) can comprise one or more components and/or characteristics of any of the other kits described in this disclosure (e.g., such as those kits depicted in FIGS. 7A-7C). For example, a kit can comprise one or more cannulas (e.g., cannula 514a and/or cannula 514b), one or more stylets, one or more drivers (e.g., as depicted in FIG. 2), one or more couplers (e.g., as depicted in FIG. 4), one or more fluid bags, one or more aspiration devices, one or more containment bags (e.g., as depicted in FIGS. 7B-7C), one or more sharps protectors (e.g., as depicted in FIGS. 7A-7B), and/or the like.

Figure 10A:
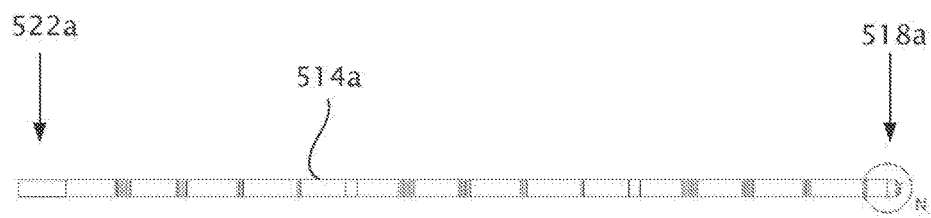
FIG. 10A depicts a side view of a cannula having a bore that is at least partially non-circular.
Figure 10B:
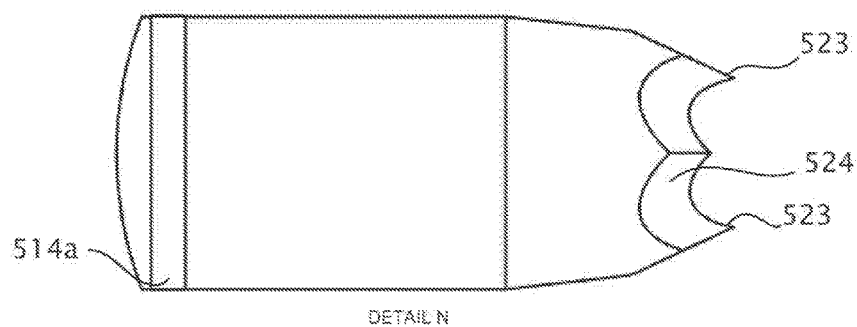
FIG. 10B depicts a side view of a portion of the cannula of FIG. 10A.
Figure 10C:
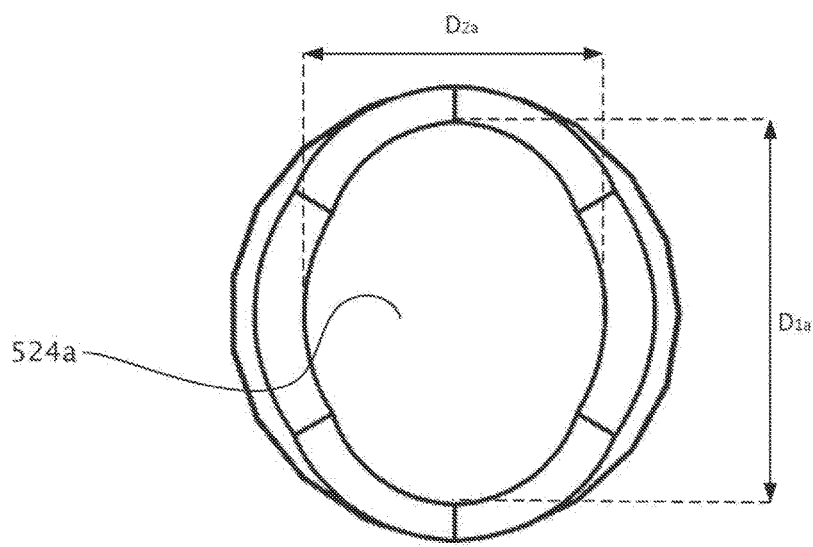
FIG. 10C depicts a front view of the cannula of FIG. 10A.
Figure 11:
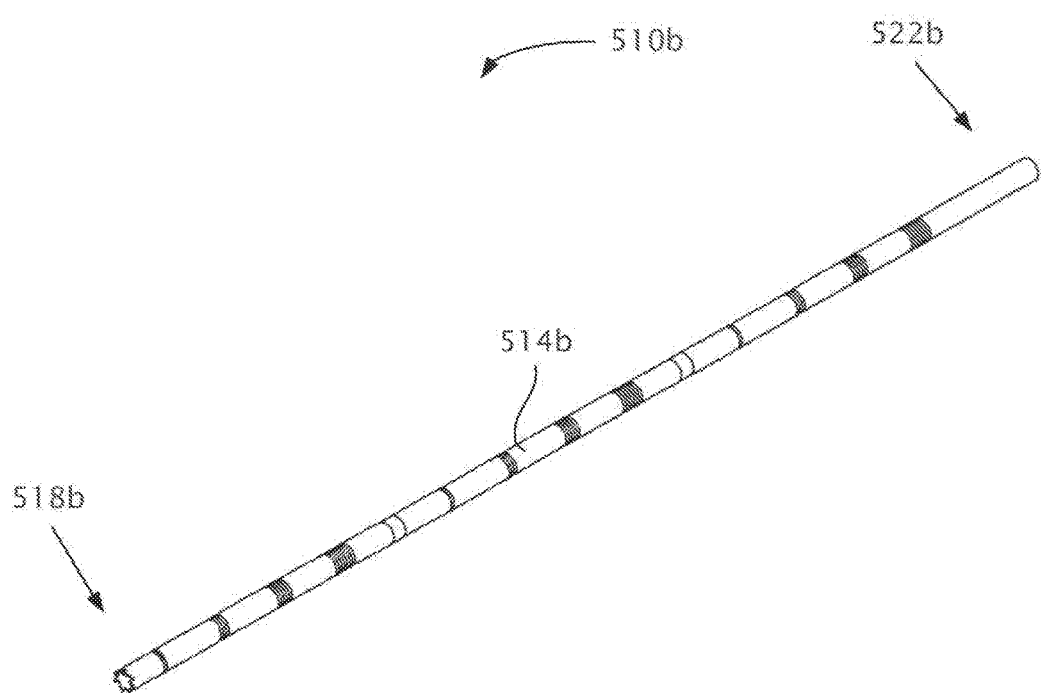
FIG. 11 depicts a perspective view of another embodiment of a cannula of the present intraosseous needle sets.
Figure 12A:
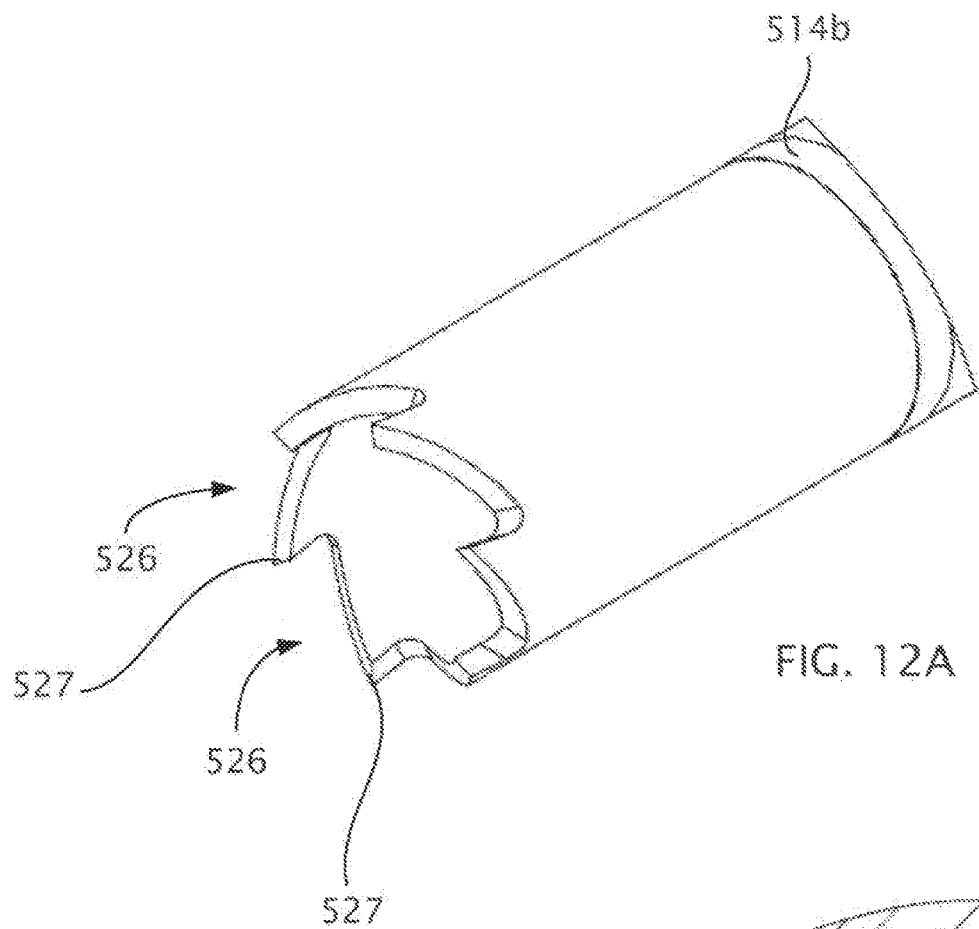
FIGS. 12A-12B depict perspective views of a portion of the cannula of FIG. 11.
Figure 12B:
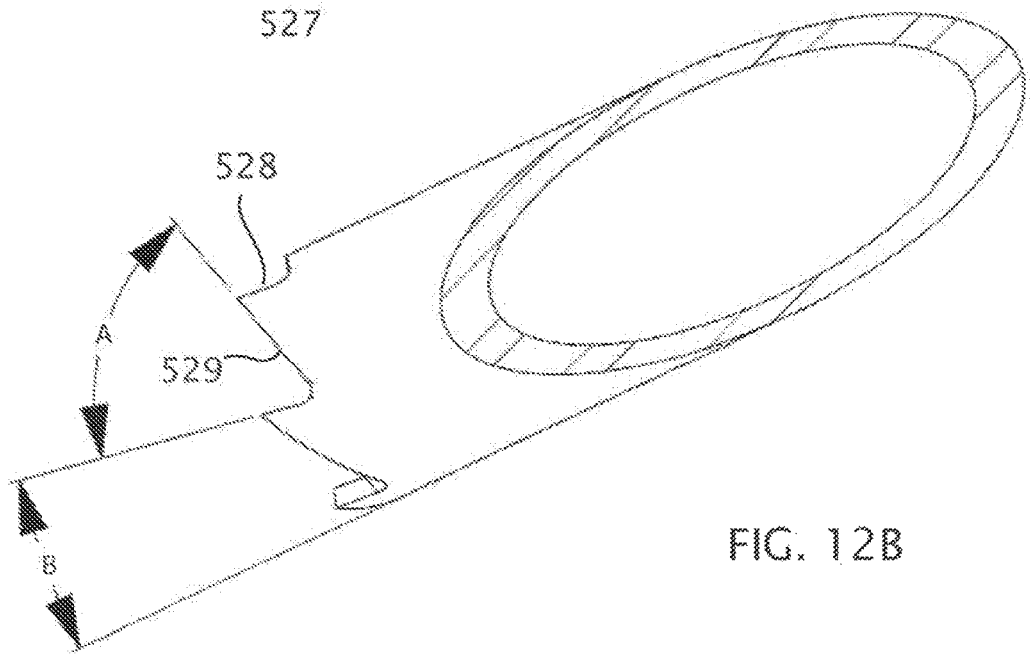
Figure 13A:
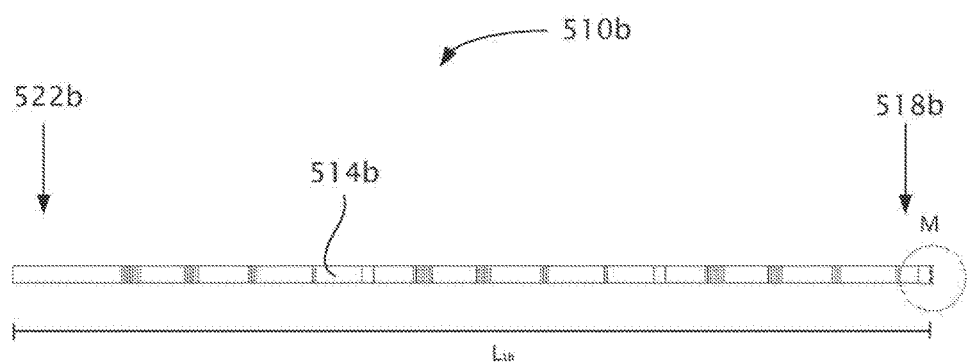
FIG. 13A depicts a side view of a cannula having a bore that is substantially circular.
Figure 13B:
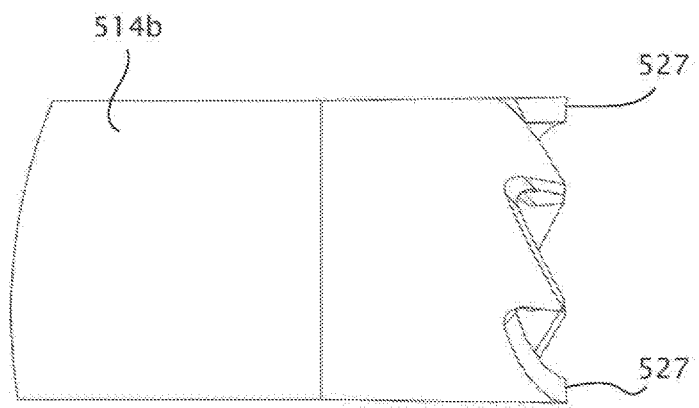
FIG. 13B depicts a side view of a portion of the cannula of FIG. 13A.
Figure 14A:
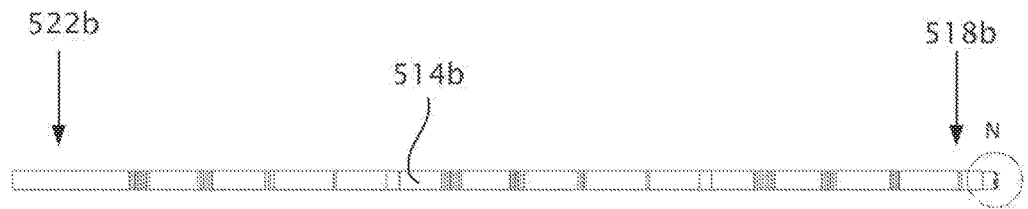
FIG. 14A depicts a side view of a cannula having a bore that is at least partially non-circular.
Figure 14B:
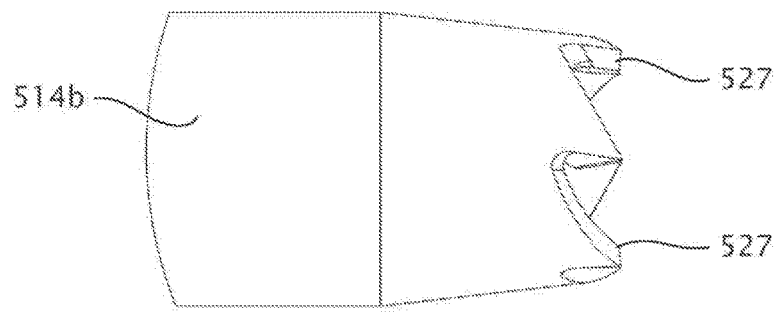
FIG. 14B depicts a side view of a portion of the cannula of FIG. 14A.
Figure 14C:
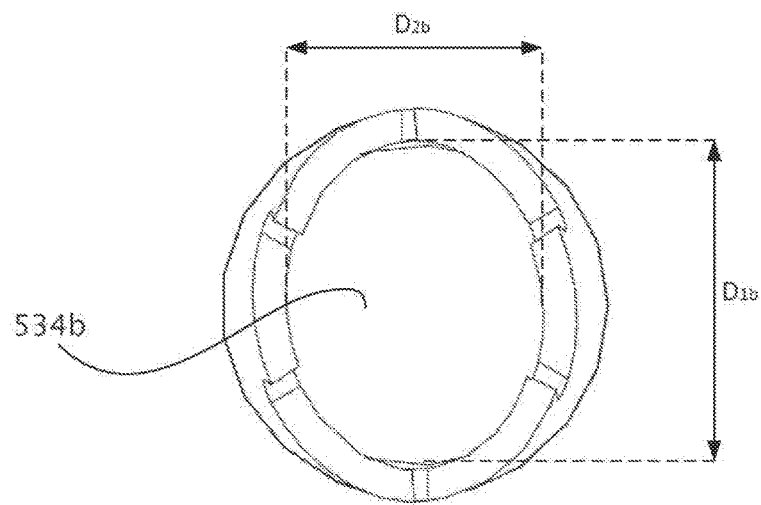
FIG. 14C depicts a front view of the cannula of FIG. 14A.

Some embodiments of the present methods include configuring a cannula cannulas 514) to have a first end (e.g., first ends 518), a second end (e.g., second ends 522), and a bore (e.g., bores 534) configured to receive a sample from a target area in a human, shaping (e.g., grinding) the first end of the cannula such that the first end comprises at least one cutting surface (e.g., plurality of crowns 523, cutting surface 524, and/or teeth 526) configured to penetrate the target area, and pinching the cannula such that a portion of the bore of the cannula comprises a circular cross-section and another portion of the bore of the cannula comprises a non-circular cross-section (e.g., as depicted in FIGS. 10A and 14A).

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

What is claimed:

1. An intraosseous needle set comprising:
a cannula having a first end, a second end, and a bore configured to receive a sample from a target area,
where the first end of the cannula is configured to penetrate the target area,
where the first end of the cannula comprises a plurality of teeth,
where at least one of the plurality of teeth comprises a first tapered surface,
where each of the plurality of teeth comprises a first side and a second side,
where a length of the first side of each tooth is less than a length of the second side.

2. The intraosseous needle set of claim 1, where each of the plurality of teeth comprises a tip defined by an intersection of the first side and the second side.

3. The intraosseous needle set of claim 2, where the tips of the plurality of teeth are disposed at an angle between 0 and 30 degrees relative to a longitudinal axis of the cannula.

4. The intraosseous needle set of claim 1, where a first side of a first tooth of the plurality of teeth intersects a second side of a second adjacent tooth of the plurality of teeth.

5. The intraosseous needle set of claim 4, wherein the first side of the first tooth and the second side of the second tooth intersect at an angle between 55 and 80 degrees.

6. The intraosseous needle set of claim 4, wherein the first side of the first tooth and the second side of the second tooth form a rounded intersection.

7. The intraosseous needle set of claim 1, where the plurality of teeth comprises at least six teeth.

8. The intraosseous needle set of claim 1, where the bore comprises:
a first section comprising a circular cross-section with a substantially constant diameter; and
a second section comprising a non-circular cross-section, where the second section is disposed closer to the first end than the second end.

9. The intraosseous needle set of claim 8, where the second section extends from the first end of the cannula toward the second end of the cannula.

10. The intraosseous needle set of claim 8, where the non-circular cross-section has a first transverse dimension and a second transverse dimension that is different than the first transverse dimension,
where the first transverse dimension is greater than the second transverse dimension.

11. The intraosseous needle set of claim 10, where a ratio of the second transverse dimension to the first transverse dimension is between 0.80 and 0.99.

12. The intraosseous needle set of claim 10, where the first transverse dimension is equal to the diameter of the circular cross-section.

13. The intraosseous needle set of claim 10, where the cannula is configured to rotatably penetrate the target area to receive a sample having a circular cross-section with a substantially constant diameter.

14. The intraosseous needle set of claim 13, where the cross-section of the sample has a transverse dimension substantially equal to the second transverse dimension of the non-circular cross-section.

15. The intraosseous needle set of claim 8, where a length of the first section of the bore is greater than a length of the second section of the bore.

16. The intraosseous needle set of claim 1, where another one of the plurality of teeth comprises a second tapered surface.

17. The intraosseous needle set of claim 16, where the second tapered surface is disposed around the bore opposite from the first tapered surface.

18. The intraosseous needle set of claim 1, where the first tapered surface extends from the first end of the cannula toward the second end of the cannula.

19. An intraosseous needle set comprising:
a cannula having a first end, a second end, and a bore configured to receive a sample from a target area,
where the first end of the cannula is configured to penetrate the target area,
where the first end of the cannula comprises a plurality of teeth,
where each of the plurality of teeth comprises a tip,
where the tips are disposed at an angle between 0 and 30 degrees relative to a longitudinal axis of the cannula.

20. An intraosseous needle set comprising:
a cannula having a first end, a second end, and a bore configured to receive a sample from a target area,
where the first end of the cannula is configured to penetrate the target area,
where the first end of the cannula comprises a plurality of teeth,
where each of the plurality of teeth comprises a first side and a second side,
where a length of the first side of each tooth is less than a length of the second side,
where a first side of a first tooth and a second side of a second adjacent tooth intersect at an angle between 55 and 80 degrees.

* * * * *